(12) United States Patent
Eguchi

(10) Patent No.: US 12,390,420 B1
(45) Date of Patent: Aug. 19, 2025

(54) COMPOSITIONS FOR TARGETED DELIVERY OF THERAPEUTIC AGENTS AND METHODS FOR THE SYNTHESIS AND USE THEREOF

(71) Applicant: BrYet US, Inc., Houston, TX (US)

(72) Inventor: Masakatsu Eguchi, Bellevue, WA (US)

(73) Assignee: BRYET US, INC., Houston, TX (US)

( * ) Notice: Subject to any disclaimer, the term of this patent is extended or adjusted under 35 U.S.C. 154(b) by 0 days.

(21) Appl. No.: 18/976,761

(22) Filed: Dec. 11, 2024

Related U.S. Application Data

(60) Provisional application No. 63/710,211, filed on Oct. 22, 2024.

(51) Int. Cl.
    *A61K 9/50* (2006.01)
    *A61K 9/48* (2006.01)
    *A61K 31/5377* (2006.01)

(52) U.S. Cl.
    CPC .......... *A61K 9/5015* (2013.01); *A61K 9/485* (2013.01); *A61K 9/5089* (2013.01); *A61K 31/5377* (2013.01)

(58) Field of Classification Search
    None
    See application file for complete search history.

(56) References Cited

U.S. PATENT DOCUMENTS

| | | |
|---|---|---|
| 7,815,936 B2 | 10/2010 | Hasenzahl et al. |
| 8,962,519 B2 | 2/2015 | Heindl et al. |
| 10,143,660 B2 | 12/2018 | Nel et al. |
| 10,874,548 B2 | 12/2020 | De Juan et al. |
| 11,224,573 B2 | 1/2022 | Yantasee et al. |
| 11,383,006 B2 | 7/2022 | Hughes et al. |
| 11,890,332 B2 | 2/2024 | Kim et al. |
| 2009/0312439 A1 | 12/2009 | Hofmann et al. |
| 2014/0309610 A1 | 10/2014 | Canham et al. |
| 2018/0344641 A1 | 12/2018 | Jeffrey et al. |
| 2019/0216736 A1 | 7/2019 | Nel et al. |
| 2021/0000744 A1 | 1/2021 | Sailor et al. |
| 2023/0241000 A1 | 8/2023 | Nel et al. |
| 2023/0398077 A1 | 12/2023 | Nel et al. |

FOREIGN PATENT DOCUMENTS

| | | |
|---|---|---|
| CN | 107349432 A | 11/2017 |
| WO | 2022223822 A1 | 10/2022 |

OTHER PUBLICATIONS

Galagudza et al. International Journal of Nanomedicine (2010), 5, pp. 231-237.*
Sonin et al. Drug Delivery (2016), 23(5), pp. 1747-1756.*
Kim et al., Biomedicines (Jan. 31, 2024), 12, 326, 24 pages.*
Castillo et al., "Mesoporous Silica Nanoparticles as Carriers for Therapeutic Biomolecules," dated May 7, 2020, 42 pages, Pharmaceutics (2020), 12, 432, 42 pages.
Mei et al. "Light-triggered Reversible Assemblies of an Azobenzene-Containing Amphiphilic Copolymer with β- Cyclodextrin Modified Hollow Mesoporus Silica Nanoparticles for Controlled Drug Release," dated Aug. 22, 2012, 3 pages, Chem. Commun. (2012), 48, 10010-10012.
Shen et al., "Cyclodextrin and Polyethylenimine Functionalized Mesoporous Silica Nanoparticles for Delivery of siRNA Cancer Therapeutic," dated Feb. 15, 2014, 11 pages, Theranostics (2014), 4 (5), 487-497.

* cited by examiner

*Primary Examiner* — Brian J Davis
(74) *Attorney, Agent, or Firm* — William R. Childs; Childs Patent Law PLLC

(57) ABSTRACT

The present disclosure provides compositions and methods for delivering therapeutic agents to particular tissues or cells in a subject. The composition disclosed herein combines unique properties of porous micro- or nano-particles with host-guest chemistry provided by functionalized silicon particle, offering a versatile approach to addressing the challenges associated with delivering therapeutic agents to target tissues or sites within the body. The present disclosure also provides a method for synthesizing a composition capable of delivering therapeutic agents to particular tissues or cells in a subject.

15 Claims, 7 Drawing Sheets

| | Loading Efficiency % | Loading Capacity % |
|---|---|---|
| C8 | 87.4 | 8.74 |
| C20 | 91.5 | 9.15 |

COMPOSITIONS FOR TARGETED DELIVERY OF THERAPEUTIC AGENTS AND METHODS FOR THE SYNTHESIS AND USE THEREOF

CROSS-REFERENCE TO RELATED APPLICATION

This U.S. Non-Provisional Application claims priority to U.S. Provisional Application No. 63/710,211, filed on Oct. 22, 2024, which is incorporated by reference in its entirety.

TECHNICAL FIELD

The present disclosure relates to compositions for targeted delivery of therapeutic agents, to a method of synthesizing such drug delivery compositions, and to a method of treating medical disorders using such drug delivery compositions. A benefit of the compositions disclosed herein can be the increased therapeutic efficacy of the therapeutic agents or drugs delivered to target cells.

BACKGROUND

Therapeutic agents, particularly cancer drugs, often suffer from limited effectiveness due to off-target effects. Targeting of a therapeutic agent, e.g., to a particular tissue or to a specific diseased tissue but not to normal tissue, is therefore desirable in the treatment of tissue specific diseases such as cancer (carcinomas, sarcomas, and so on). Targeted drug delivery can provide maximum therapeutic activity, reduce overall doses required for treatment, and limit toxicities in non-target tissues. However, targeted site-specific delivery of therapeutic agents requires an effective system design. Further, the release profile of therapeutic agents to maintain an effective drug concentration at a target site after the drug enters the body can greatly affect the efficacy of therapeutic agents. Thus, delivery of a therapeutic agent at a specific target tissue or site within the body has been a persistent challenge in the field of pharmaceutical technology.

There is a need to develop new and improved compositions for delivering therapeutic agents at an adequate concentration to target tissues or cells.

SUMMARY

The present disclosure provides compositions and methods for delivering therapeutic agents to particular tissues or cells in a subject. The present disclosure also provides methods for synthesizing a composition capable of selectively delivering therapeutic agents to target tissues or cells, such as diseased tissues or cells, in a subject.

In some embodiments, the present disclosure provides a composition for delivery of an active agent to a cell in a target tissue of a subject in need thereof. In some embodiments, the composition includes: an active agent; and a porous particle, wherein the porous particle comprises a plurality of microscale reservoirs and a host molecular structure is adhered to a surface of the porous particle. In some embodiments, the host molecular structure has a structure of Formula 1, wherein:

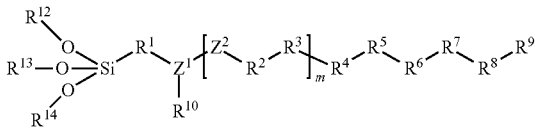

Formula 1

$R^1$ is —$(C_1-C_6)$alkylene-, or —H;
$Z^1$ is —(N—)—, —H, or none;
$Z^2$ is —(C(=O))—, $SO_2$, or none;
$R^2$ is —(C(—H)—$R^{11}$)—, —$(C_1-C_3)$alkylene, —(C(—H)—$((C_1-C_6)$alkylene-(C(=O)(—O⁻X))))—, —(C(—H)(—$(C_1-C_6)$alkylene-Ar¹)), —O—, —H, or none;
$R^3$ is —$(CH_2)$—, —(N(—H))—, —H, or none;
$R^4$ is —$(CH_2)$—, —(C(=O))—, —H, or none;
$R^5$ is —$(C_1-C_{20})$alkylene-, —$(C_1-C_3)$alkylene-Ar², —O—, —H, or none;
$R^6$ is —$(CH_2)$—, —H, or none;
$R^7$ is —$(CH_2)$—, —(C(=O))—, —H, or none;
$R^8$ is —$(CH_2)$—, —(N(—H))—, —H, or none;
$R^9$ is —$(C_1-C_3)$alkylene-Ar², —(C(=O)(—O⁻X)), $(C_1-C_{20})$alkylene-(C(=O)(—O⁻X)), $(C_1-C_{20})$alkyl, —H, or none;
$R^{10}$ is —$(C_1-C_6)$alkyl, or —H;
$R^{11}$ is side chain of amino acid such as methyl group (—$CH_3$), guanidino group (—$(CH_2)_3$—NH—C(=NH)—$NH_2$), amide group (—$CH_2$—$CONH_2$), (—$CH_2$—$CH_2$—$CONH_2$), carboxyl group (—$CH_2$—COOH), (—$CH_2$—$CH_2$—COOH), thiol group (—$CH_2$—SH), amide group (—$CH_2$—$CH_2$—$CONH_2$), carboxyl group (—$CH_2$—$CH_2$—COOH), hydrogen atom (—H), imidazole group (—$CH_2$—$C_3H_3N_2$), sec-butyl group (—$CH(CH_3)$—$CH_2$—$CH_3$), isobutyl group (—$CH_2$—$CH(CH_3)_2$), amino group (—$(CH_2)_4$—$NH_2$), (—$(CH_2)_3$—$NH_2$), thioether group (—$CH_2$—$CH_2$—S—$CH_3$), hydroxymethyl group (—$CH_2$—OH), hydroxyethyl group (—CH(OH)—$CH_3$), hydroxyphenyl group (—$CH_2$—$C_6H_4$—OH), isopropyl group (—$CH(CH_3)_2$), or their derivative;
m is 0-150;
provided that if m>2, then Ar¹ or $R^{11}$ can be chosen independently;
Ar¹ is a substituted phenyl, an unsubstituted phenyl, a substituted indole, or an unsubstituted indole;
Ar² is a substituted phenyl, an unsubstituted phenyl, a substituted naphthyl, an unsubstituted naphthyl, a substituted indole, or an unsubstituted indole; and
X is H⁺, Na⁺, Ca⁺, or K⁺, and
$R^{12}$, $R^{13}$, and $R^{14}$, each independently, represents the surface of the porous particle or an adjacent silane. In some embodiments of the composition:
$Z^1$ is —(N—)—;
$Z^2$ is —(C(=O))—;
$R^2$ is —(C(—H)(—$(C_1-C_6)$alkylene-Ar¹)) and Ar¹ is an unsubstituted phenyl;
$R^3$ is —(N(—H))—;
$R^4$ is —(C(=O))—;
$R^9$ is —$(C_1-C_{20})$alkylene-(C(=O)(—O⁻X)); and
$R^{10}$ is —H.
In some embodiments of the composition:
$Z^1$ is —(N—)—;
$Z^2$ is —(C(=O))—;
$R^2$ is —(C(—H)—$((C_1-C_6)$alkylene-(C(=O)(—O⁻X))))—;
$R^3$ is —(N(—H))—;

$R^4$ is —(C(=O))—;
$R^7$ is —(C(=O))—;
$R^9$ is —($C_1$-$C_3$)alkylene-$Ar^2$ and $Ar^2$ is an unsubstituted phenyl; and
$R^{10}$ is —H.

In some embodiments of the composition:
$Z^1$ is —(N—)—;
$Z^2$ is —(C(=O))—;
$R^9$ is —($C_1$-$C_3$)alkylene-$Ar^2$, —(C(=O)(—O⁻X)), ($C_1$-$C_{20}$)alkylene-(C(=O)(—O⁻X)), or ($C_1$-$C_{20}$)alkyl; and
$R^{10}$ is —H.

In some embodiments, the host molecular structure has a structure of Formula 2, Formula 3, Formula 4, or Formula 5, or mixture thereof:

Formula 2

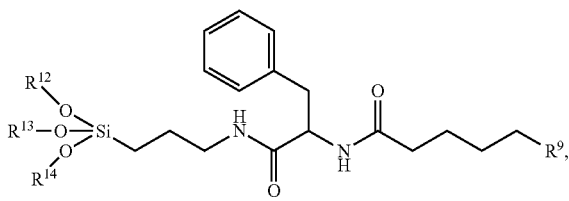

wherein $R^9$ is —($C_1$-$C_{20}$)alkylene-(C(=O)(—O⁻X));

Formula 3

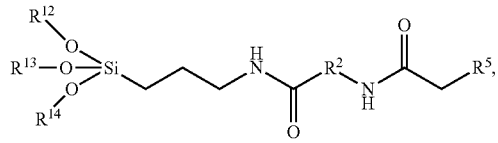

wherein $R^2$ is —(C(—H)—((C_1$-$C_6$)alkylene-(C(=O)(—O⁻X)))) and $R^5$ is —($C_1$-$C_3$)alkylene-$Ar^2$;

Formula 4

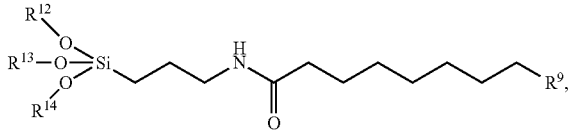

wherein $R^9$ is —($C_1$-$C_{20}$)alkyl; and

Formula 5

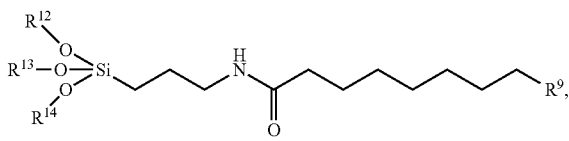

wherein $R^9$ is —($C_1$-$C_{20}$)alkylene-(C(=O)(—O⁻X));
wherein $R^{12}$, $R^{13}$, and $R^{14}$, each independently, represents the surface of the porous particle or an adjacent silane.

In some embodiments, the porous particle is a micro or a nano particle. In some embodiments, the porous particle is biocompatible and degradable. In some embodiments, the plurality of microscale reservoirs of the porous particle has a size ranging from about 0.3 μm to about 4 μm. In some embodiments, the porous particle has a shape selected from the group consisting of discoidal, spheroid, non-spheroid, oblate spheroid, and combinations thereof. In some embodiments, the porous particle includes a porous oxide material or a porous etched material. In some embodiments, the porous particle is able to overcome at least one biological barrier.

In some embodiments, the porous particle includes a porous oxide material selected from the group consisting of porous silica, porous aluminum oxide, porous titanium oxide, porous iron oxide, and combinations thereof. In some embodiments, the porous particle includes a porous etched material selected from the group consisting of porous silicon, porous silica, porous germanium, porous GaAs, porous InP, porous SiC, porous $Si_xGe_{1-x}$, porous GaP, porous GaN, and combinations thereof.

In some embodiments, the active agent includes a kinase inhibitor. In some embodiments, the surface of the porous particle includes an interior surface of a pore of the porous particle. In some embodiments, the active agent is retained for a longer duration at a retention pH by a porous particle having the molecular host structure than a porous particle or a porous particle that excludes the molecular host structure. In some embodiments, the active agent forms a non-covalent complex with the molecular host structure.

In some embodiments, the present disclosure provides a method of synthesizing a composition for delivery of an active agent to a cell in a target tissue of a subject in need thereof.

In some embodiments, the method includes: providing a porous particle, wherein the porous particle comprises a plurality of microscale reservoirs and a host molecular structure is adhered to a surface of the porous particle; providing an active agent; and mixing the active agent with the porous particle in a liquid medium. In some embodiments of the method, the host molecular structure has a structure of Formula 1,
wherein:

Formula 1

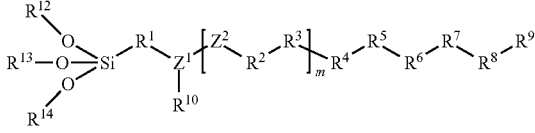

$R^1$ is —($C_1$-$C_6$)alkylene-, or —H;
$Z^1$ is —(N—)—, —H, or none;
$Z^2$ is —CO—, $SO_2$, or none;
$R^2$ is —(C(—H)—$R^{11}$)—, —($C_1$-$C_3$)alkylene, —(C(—H)—(($C_1$-$C_6$)alkylene-(C(=O)(—O⁻X))))—, —(C(—H)(—($C_1$-$C_6$)alkylene-$Ar^1$)), —O—, —H, or none;
$R^3$ is —($CH_2$)—, —(N(—H))—, —H, or none;
$R^4$ is —($CH_2$)—, —(C(=O))—, —H, or none;
$R^5$ is —($C_1$-$C_{20}$)alkylene-, —($C_1$-$C_3$)alkylene-$Ar^2$, —O—, —H, or none;
$R^6$ is —($CH_2$)—, —H, or none;
$R^7$ is —($CH_2$)—, —(C(=O))—, —H, or none;
$R^8$ is —($CH_2$)—, —(N(—H))—, —H, or none;
$R^9$ is —($C_1$-$C_3$)alkylene-$Ar^2$, —(C(=O)(—O⁻X)), ($C_1$-$C_{20}$)alkylene-(C(=O)(—O⁻X)), —($C_1$-$C_{20}$)alkyl, —H, or none;
$R^{10}$ is —($C_1$-$C_6$)alkylene, or —H;

R¹¹ is side chain of amino acid such as methyl group (—CH₃), guanidino group (—(CH₂)₃—NH—C(=NH)—NH₂), amide group (—CH₂—CONH₂), (—CH₂—CH₂—CONH₂), carboxyl group (—CH₂—COOH), (—CH₂—CH₂—COOH), thiol group (—CH₂—SH), amide group (—CH₂—CH₂—CONH₂), carboxyl group (—CH₂—CH₂—COOH), hydrogen atom (—H), imidazole group (—CH₂—C₃H₃N₂), sec-butyl group (—CH(CH₃)—CH₂—CH₃), isobutyl group (—CH₂—CH(CH₃)₂), amino group (—(CH₂)₄—NH₂), (—(CH₂)₃—NH₂), thioether group (—CH₂—CH₂—S—CH₃), hydroxymethyl group (—CH₂—OH), hydroxyethyl group (—CH(OH)—CH₃), hydroxyphenyl group (—CH₂-C₆H₄—OH), isopropyl group (—CH(CH₃)₂), or their derivative;

m is 0~150;

provided that if m>2, then Ar¹ or R¹¹ can be chosen independently;

Ar¹ is a substituted phenyl, an unsubstituted phenyl, a substituted indole, or an unsubstituted indole;

Ar² is a substituted phenyl, an unsubstituted phenyl, a substituted naphthyl, an unsubstituted naphthyl, a substituted indole, or an unsubstituted indole; and X is H⁺, Na⁺, Ca⁺, or K⁺, and wherein R¹², R¹³, and R¹⁴, each independently, represents the surface of the porous particle or an adjacent silane.

In some embodiments, the method of synthesizing a composition according to the present disclosure further includes: providing the host molecular structure of Formula 1 by reacting a molecular structure of Formula 6 with a molecule of Formula 7, wherein Formula 6

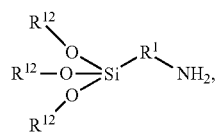

Formula 7

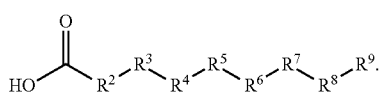

In some embodiments, the method includes providing the host molecular structure of Formula 1 by reacting a molecular structure of Formula 6 with a molecule of Formula 7 is performed in the presence of a carbodiimide or another peptide coupling reagent.

In some embodiments, the method of synthesizing a composition according to the present disclosure further includes: providing the host molecular structure having a structure of Formula 1 by reacting a molecule of Formula 8 with the surface of the porous particle, Formula 8

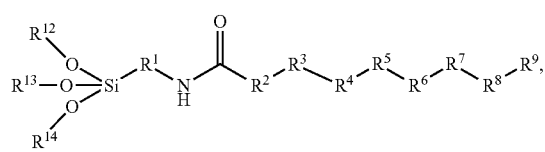

wherein R¹² is a (C₁-C₃)alkyl.

In some embodiments, the present disclosure provides a method of treating a medical disorder in a subject in need thereof, which includes: administering to the subject in need thereof a composition, wherein the composition includes an active agent; and a porous particle, wherein the porous particle comprises a plurality of microscale reservoirs and a host molecular structure is adhered to a surface of the porous particle. In some embodiments of the method, the host molecular structure has a structure of Formula 1, wherein:

Formula 1

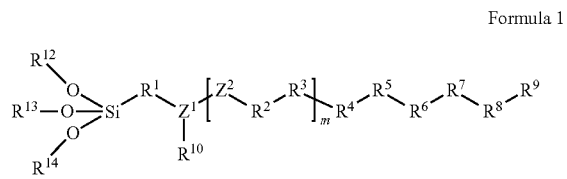

R¹ is —(C₁-C₆)alkylene-, or —H;

Z¹ is —(N—)—, —H, or none;

Z² is —CO—, —SO₂—, or none;

R² is —(C(—H)—R¹¹)—, —(C₁-C₃)alkylene, —(C(—H)—((C₁-C₆)alkylene-(C(=O)(—O—X))))—, —(C(—H)(—(C₁-C₆)alkylene-Ar¹)), —O—, —H, or none;

R³ is —(CH₂)—, —(N(—H))—, —H, or none;

R⁴ is —(CH₂)—, —(C(=O))—, —H, or none;

R⁵ is —(C₁-C₂₀)alkylene, —(C₁-C₃)alkylene-Ar², —O—, —H, or none;

R⁶ is —(CH₂)—, —H, or none;

R⁷ is —(CH₂)—, —(C(=O))—, —H, or none;

R⁸ is —(CH₂)—, —(N(—H))—, —H, or none;

R⁹ is —(C₁-C₃)alkylene-Ar², —(C(=O)(—O⁻X)), (C₁-C₂₀)alkylene-(C(=O)(—O⁻X)), —(C₁-C₂₀)alkyl, —H, or none;

R¹⁰ is —(C₁-C₆)alkylene, or —H;

R¹¹ is side chain of amino acid such as methyl group (—CH₃), guanidino group (—(CH₂)₃—NH—C(=NH)—NH₂), amide group (—CH₂—CONH₂), (—CH₂—CH₂—CONH₂), carboxyl group (—CH₂—COOH), (—CH₂—CH₂—COOH), thiol group (—CH₂—SH), amide group (—CH₂—CH₂—CONH₂), carboxyl group (—CH₂—CH₂—COOH), hydrogen atom (—H), imidazole group (—CH₂—C₃H₃N₂), sec-butyl group (—CH(CH₃)—CH₂—CH₃), isobutyl group (—CH₂—CH(CH₃)₂), amino group (—(CH₂)₄—NH₂), (—(CH₂)₃—NH₂), thioether group (—CH₂—CH₂—S—CH₃), hydroxymethyl group (—CH₂—OH), hydroxyethyl group (—CH(OH)—CH₃), hydroxyphenyl group (—CH₂—C₆H₄—OH), isopropyl group (—CH(CH₃)₂), or their derivative;

m is 0~150;

provided that if m>2, then Ar¹ or R¹¹ can be chosen independently;

Ar¹ is a substituted phenyl, an unsubstituted phenyl, a substituted indole, or an unsubstituted indole;

Ar² is a substituted phenyl, an unsubstituted phenyl, a substituted naphthyl, an unsubstituted naphthyl, a substituted indole, or an unsubstituted indole; and X is H⁺, Na⁺, Ca⁺, or K⁺, and wherein R¹², R¹³, and R¹⁴, each independently, represents the surface of the porous particle or an adjacent silane.

In some embodiments of the compositions or methods disclosed herein, the active agent includes a kinase inhibitor selected from the group consisting of Abemaciclib, Abrocitinib, Acalabrutinib, Afatinib, Alectinib, Almonertinib, Alpelisib, Amivantamab, Apatinib, Asciminib, Avapritinib, Axitinib, Baricitinib, Binimetinib, Bosutinib, Brigatinib, Cabozantinib, Capivasertib, Capmatinib, Catequentinib, Ceritinib, Cetuximab, Cobimetinib, Copanlisib, Crizotinib, Dabrafenib, Dacomitinib, Dasatinib, Defactinib, Delgocitinib, Deucravacitinib, Duvelisib, Encorafenib, Entrectinib, Erdafitinib, Erlotinib, Everolimus, Fasudil, Fedratinib, Filgotinib, Flumatinib, Fostamatinib, Fostamatinib, Fruquintinib, Furmonertinib, Futibatinib, Gefitinib, Gilteritinib, Ibrutinib, Icotinib, Idelalisib, Imatinib, Infigratinib, Ivosidenib, Lapatinib, Larotrectinib, Lazertinib, Leniolisib, Lenvatinib, Lorlatinib, Margetuximab, Midostaurin, Mobocertinib, Necitumumab, Neratinib, Netarsudil, Nilotinib, Nimotuzumab, Nintedanib, Olaratumab, Olmutinib, Orelabrutinib, Osimertinib, Pacritinib, Palbociclib, Panitumumab, Paxalisib, Pazopanib, Peficitinib, Pemigatinib, Pertuzumab, Pexidartinib, Pirtobrutinib, Ponatinib, Pralsetinib, Pyrotinib, Quizartinib, Radotinib, Ramucirumab, Regorafenib, Ribociclib, Ripasudil, Ripretinib, Ritlecitinib, Ruxolitinib, Savolitinib, Selpercatinib, Selumetinib, Simotinib, Sirolimus, Sorafenib, Sotorasib, Sunitinib, Surufatinib, Temsirolimus, Tenalisib, Tepotinib, Tirabrutinib, Tirbanibulin, Tivozanib, Tofacitinib, Trametinib, Trastuzumab, Trilaciclib, Tucatinib, Umbralisib, Upadacitinib, Vandetanib, Vemurafenib, Volasertib, Zanubrutinib, and mixtures thereof.

In some embodiments of the compositions or methods disclosed herein, the medical disorder is selected from the group consisting of Atopic dermatitis, Mantle cell lymphoma, NSCLC with EGFR mutations, NSCLC with ALK translocations, Advanced mutation+ve NSCLC, Breast cancer, HR+ve, HER2-ve, NSCLC, Gastric cancer, NSCLC, Chronic myelogenous leukemia, PDGFR exon 18 mutation (incl D842V)+ve, Renal Cell Carcinoma, Rheumatoid arthritis, BRAF mutant melanoma, Chronic Myelogenous Leukemia, ALK-rearranged metastatic NSCLC, Medullary Thyroid Cancer, HR+ and PI3K mutation breast cancer, MET mutation+ve NSCLC, EGFR colorectal cancer, Melanoma, breast cancer, Follicular lymphoma, NSCLC with Alkmutation, Skin cancer, NSCLC with EGFR mutations, Chronic Myelogenous Leukemia, Solid tumors, Psoriasis, CLL, SLL, FL, BRAF mutant melanoma, ROS1+ve NSCLC, solid tumors NTRK+ve, Advanced metastatic urothelial carcinoma, Pancreatic Cancer, Renel Cell Carcinoma, Cerebral Vasospasm PAH, myelofibrosis, Rheumatoid arthritis, Chronic myelogenous leukemia, Autoimmune thrombocytopenia, Chronic immune thrombocytopenia, Metastatic colorectal cancer, Cholangiocarcinoma, Acute myeloid leukemia FLT3 mutant, Mantle cell lymphoma, chronic lymphocytic leukemia, Chronic Myelogenous Leukemia, Acute myeloid leukemia (AML), Breast Cancer, Solid tumours with NTRK fusions, Activated phosphoinositide 3-kinase delta syndrome (APDS), PASLI (p110 delta activating mutation causing senescent T cells), lymphadenopathy, immunodeficiency, Thyroid cancer (DTC) kidney cancer, ALK+ve met NSCLC, MHER2-positive breast cancer, Acute myeloid leukemia (FLT3 mutation-positive), NSCLC with EGFR mutations, HER2-positive breast cancer, Glaucoma (topical), Chronic Myelogenous Leukemia, cell carcinomas of the head and neck, Idiopathic pulmonary fibrosis, Soft tissue sarcoma, T790M+ve NSCLC, mantle cell lymphoma CLL, SLL, T790M+ve NSCLC, Myelofibrosis, Advanced (metastatic) breast cancer, EGFR colorectal cancer, Malignant glioblastoma, Renal cancer, Rhematoid arthritis, Cholangiocarcinoma with FGFR2 fusionA, HER2-positive breast cancer, Tenosynovial giant cell tumor, Mantle Cell Lymphoma, Chronic Myelogenous Leukemia, ALL, Met RET fusion+ve NSCLC MTC, Breast cancer, Acute myeloid leukemia, Chronic Myelogenous Leukemia, MNSCLC colorectal cancer, Clorectal Cancer GIST, HCC, Advanced (metastatic) breast cancer HR+ve, HER2-ve, Glaucoma ocular hypertension, Advanced GIST Mastocytosis, Severe alopecia, Myelofibrosis, Adenocarcinoma, NSCLC, NSCLC, MTC, thyroid cancers, Neurofibromatosis type 1, Solid tumors, kidney Transplantation, Renal Cancer HCC, KRAS non-small-cell lung cancer, Renal Cancer, Imatinib resistant GIST, Advanced pancreatic NET, Advanced Renal Cell Carcinoma, PTCL, breast cancer, Metastatic NSCLC, Chronic myelogenous leukemia, Actinic keratosis, Advanced RCC, Rheumatoid arthritis, M-Melanoma with BRAFV600E, EGFR breast cancer, SCLC chemo myelo preservation, HER2-positive breast cancer, Marginal zone lymphoma, Rheumatoid arthritis, Thyroid Cancer, Metastatic Melanoma BRAFV600E, Acute myeloid leukemia, and mantle cell lymphoma.

In some embodiments, the method further includes: releasing the active agent within a cell in a target tissue by passing the composition into an interior of the target tissue. In some embodiments, the method further includes a cell in a target tissue is a cancer cell or a cell located within a tumor.

BRIEF DESCRIPTION OF THE DRAWINGS

The foregoing summary, as well as the following detailed description of the embodiments, will be better understood when read in conjunction with the attached drawings. For the purpose of illustration, there are shown in the drawings some embodiments, which can be preferable. It should be understood that the embodiments depicted are not limited to the precise details shown. Unless otherwise noted, the drawings are not to scale.

DETAILED DESCRIPTION

Figure 1:
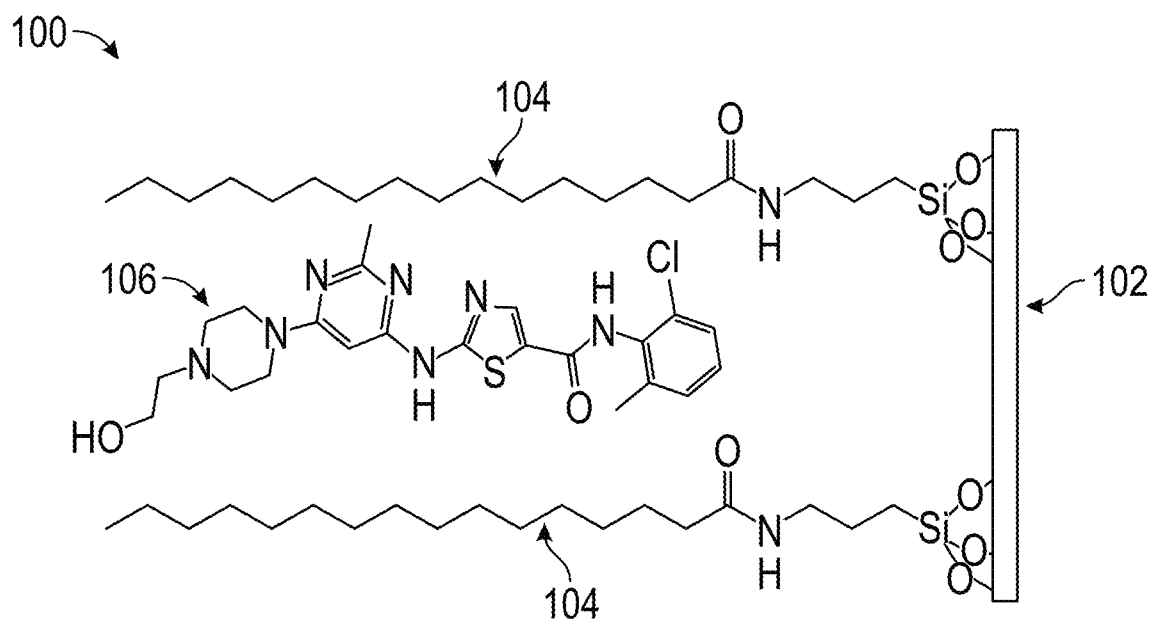
FIG. 1 is a Lewis structure or molecular representation of an embodiment of a composition including an embodiment of host molecular structure and dasatinib as an embodiment of an active agent.

Unless otherwise noted, all measurements are in standard metric units.

Unless otherwise noted, all instances of the words "a," "an," or "the" can refer to one or more than one of the words that they modify.

Unless otherwise noted, the phrase "at least one of" means one or more than one of an object. For example, "at least one of the two or more gas pipes have a pipe proximal end connected to the manifold section and a pipe distal end that terminates in a threaded joint" means a single gas pipe, a two gas pipes, three gas pipes, four or more gas pipes, or any combination thereof.

Unless otherwise noted, the term "about" refers to ±10% of the non-percentage number that is described, rounded to the nearest number to the accuracy shown. For example, about 105.3 mm, would include 94.8 to 115.8 mm. Unless otherwise noted, the term "about" refers to ±5% of a percentage number. For example, about 20% would include 15 to 25%. When the term "about" is discussed in terms of a range, then the term refers to the appropriate amount less than the lower limit and more than the upper limit. For example, from about 100 to about 200 mm would include from 90 to 220 mm.

Unless otherwise noted, the terms "provide", "provided" or "providing" refer to the supply, production, purchase, manufacture, assembly, formation, selection, configuration, conversion, introduction, addition, or incorporation of any element, amount, component, reagent, quantity, measurement, or analysis of any method or system of any embodiment herein.

Unless otherwise noted, properties (height, width, length, ratio, pressure, temperature etc.) as described herein are understood to be averaged measurements with respect to accuracy and significant digits.

Unless otherwise noted, when a range of numbers refers to numbers that are easily and routinely varied in a laboratory setting, such as weight, mass, concentration, temperature, charge density, or pressure, then the range of numbers or measurements includes all numbers in that range. For example, the range of 100 mA/cm$^2$ to about 200 mA/cm$^2$ includes 105, 110, 120, 130, 140, 150, 160, 170, 180, 190 and any sub range/number therein.

Unless otherwise noted, the term "for example" or "e.g.," as used herein, is used merely by way of example, and should not be construed as limiting the present disclosure to only those items explicitly referred to in the specification.

Unless otherwise noted, the term "microparticle" means a particle having a maximum characteristic size of less than 1000 microns and a minimum characteristic size of greater than 50 nm.

Unless otherwise noted, the term "nanoparticle" means a particle having a maximum characteristic size of from 1 micron to 20 nm.

Unless otherwise noted, "micron" means "micrometer" and the term "microns" means "micrometers." These terms are interchangeable.

Unless otherwise noted, the term "microscale reservoirs" refers to pores with an average size of less than 1000 microns.

Unless otherwise noted, "nanoporous" or "nanopores" refer to pores with an average size of less than 1 micron.

Unless otherwise noted, "porous particle" refers to particles having a maximum characteristic size of less than about 1000 microns, or less than about 100 microns, preferably less than about 10 microns. The porous particle of the present disclosure should have a relatively high porosity to enable loading of the active agent and host molecular structure in the pores of the porous particle.

Unless otherwise noted, "biocompatible" refers to a material that can be degraded under physiological conditions by physiological enzymes and/or chemical conditions.

Unless otherwise noted, "biodegradable" refers to a material that can dissolve or degrade in a physiological medium.

Unless otherwise noted, the terms "therapeutic agent", "active agent", "active ingredient", "active pharmaceutical ingredient", "active drug" or "drug" as used herein are used interchangeably and are defined to mean any active pharmaceutical ingredient ("API"), including its pharmaceutically acceptable salts (non-limiting examples of which include inorganic salts such as the hydrochloride salts, the hydrobromide salts and the hydroiodide salts, and organic salts such as acetate, maleate, fumarate, tartrate, citrate, methane sulfonate and ethane sulfonate), as well as the anhydrous, hydrated, and solvated forms, polymorphs, prodrugs, and the individually optically active enantiomers of the API. The active drug includes the molecule or ion and the appended portions of the molecule that cause the drug to be an ester or salt of the molecule.

Unless otherwise noted, the terms "composition", "drug delivery composition", "drug delivery system" and "dosage form" as used herein are used interchangeably and are defined to mean a pharmaceutical composition, preparation or system in which doses of medicine or active agent are included. Compositions or dosage forms can be administered by any route of administration known to persons skilled in the art, including but not limited to oral, rectal, and vaginal administration, and parenteral, including intradermal (IM), subcutaneous (SQ), intramuscular (IM), and intravenous (IV).

Unless otherwise noted, the terms "controlled release" or compositions which deliver an active agent at a "controlled rate" as used herein refer to a property of a composition wherein absorption and bioavailability of the active agent in the composition is maintained such that therapeutically effective amounts of the active agent are bioavailable over an extended period.

Unless otherwise noted, the terms "treat", "treating", and "treatment" are used interchangeably and are meant to indicate a postponement of development of a disorder and/or a reduction in the severity of symptoms that will or are expected to develop. The terms further include ameliorating existing symptoms, and ameliorating the underlying metabolic causes of symptoms.

Unless otherwise noted, the terms "subject" and "patient" as used herein are used interchangeably and mean all members of the animal kingdom (e.g. humans).

Unless otherwise noted, the term "individual" (as in the subject of the treatment) means both mammals and non-mammals. Mammals include, for example, humans; non-human primates, e.g. apes and monkeys; cattle; horses; sheep; and goats. Non-mammals include, for example, fish and birds.

Unless otherwise noted, the expression "effective amount", when used to describe therapy to an individual suffering from a cancer or other cellular proliferative disorder, refers to the amount of a composition that inhibits the abnormal growth or proliferation, or alternatively induces apoptosis of cancer cells, preferably tumor cells, resulting in a therapeutically useful and selective cytotoxic effect on proliferative cells.

Unless otherwise noted, the term "cellular proliferative disorder" means a disorder wherein unwanted cell proliferation of one or more subsets of cells in a multicellular organism occurs. In some such disorders, cells are made by the organism at an atypically accelerated rate.

The term "alkyl", by itself or as part of another substituent means, unless otherwise stated, a straight, branched or cyclic chain hydrocarbon having the number of carbon atoms designated (i.e. $C_1$-$C_{20}$ means one to twenty carbons) and includes straight, branched chain, or cyclic groups. Examples include: methyl, ethyl, propyl, isopropyl, butyl, isobutyl, tert-butyl, pentyl, neopentyl, hexyl, cyclohexyl and cyclopropylmethyl.

The term "alkylene", by itself or as part of another substituent means, unless otherwise stated, a divalent straight, branched, or cyclic chain hydrocarbon.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution can be at any chemically accessible position. Where a substituent is an alkyl or alkoxy group, the carbon chain can be branched, straight or cyclic, with straight being preferred.

Unless otherwise noted, all reactions, procedures, and formulations were or can be performed under normal temperature and pressure, namely 20° C. and 1 atmosphere (101.3 kPa).

Unless otherwise noted, all elements can be abbreviated using their atomic symbol, e.g., oxygen can be shown as 0, hydrogen as H, and platinum can be shown at Pt.

Therapeutic agents, especially cancer drugs, delivered using conventional drug delivery systems pose several challenges, such as limited effectiveness due to inadequate drug delivery, low drug concentration at the target site, side effects due to multitarget interactions, and unwanted interactions of drug with bioenvironmental factors that affect drug access to targeted sites in the body. Conventional porous particles rely on ranges of particle size, pore size and/or crude surface wettability agents to provide a measure of selective delivery of therapeutic agents.

Compositions are disclosed herein which solve or ameliorate the above-mentioned problems associated with conventional drug delivery systems by selectively targeting therapeutic agents to desired tissues or cells. It has been discovered that combining or pairing therapeutic agents with porous particles having functionalized surface molecules can produce a host-guest relationship. It has been further discovered that these host-guest relationships can control the release profiles or kinetics of the therapeutic agents from the porous particles. The ability to combine particle size, particle shape, particle pore size, and the host-guest non-convent interactions represents a powerful platform for tailoring drug delivery compositions with specific therapeutic agent.

The disclosed composition combines unique properties of porous micro- or nano-particles with host-guest chemistry provided by functionalized silicon particle, offering a versatile approach to addressing the challenges associated with delivering therapeutic agents to target tissues or cells within the body. The composition disclosed herein includes porous particles of micrometer or nanometer size having adhered to its external surface and/or interior pore surface a functionalized silicon particle which acts as a "host" for a given therapeutic agent, resulting in a host-guest complex. The host-guest system can control the release profile of therapeutic agents based on the type of, number of, and spacing of polar, nonpolar groups, and/or ionic groups (pH dependent) to allow for hydrogen bonding, van der Waals interactions, and/or ionic bonding to speed, slow, or make pH dependent the desorption profile of the therapeutic agents from the porous particles. The composition disclosed herein is capable of targeting therapeutic agents to a particular tissue or cell type and releasing therapeutic agents at the target site. Therefore, the disclosed composition can result in a high local drug concentration at the target site and relatively low drug concentration in systemic organs, relative to non-target administration of the same therapeutic agent. This higher local concentration of the therapeutic agents local to target cells and issues can improve the effectiveness of therapeutic agents, especially those used in cancer therapy, while minimizing side effects, and reducing damages to normal tissues and cells. The porous particle having the host-guest complex can retain a therapeutic agent for a longer duration than a porous particle that excludes the host-guest complex and release it at the target site at a controlled rate in order to maintain full drug efficacy. In some embodiments, the selection of the host molecules can tailor the type of, number of, and spacing of polar, nonpolar groups, and/or ionic groups (pH dependent) to provide improved release profiles for a specific therapeutic agent "guest" molecules, relative to other host molecules for the same therapeutic agent. In general, more host guest interactions based on hydrogen bonding, van der Waals interactions, and/or ionic bonding tend to result in longer release profiles.

Referring to FIG. 1, there is shown an embodiment of the composition 100 that can be used to deliver the active agent, dasatinib, to a cell in a target tissue of a subject in need thereof. In this embodiment, the composition 100 includes a porous silicon nanoparticle having a pore surface 102 and a functionalized silane host 104 adhered to surface 102 of a pore of the porous particle. The composition 100 also includes dasatinib 106 as a guest which is non-covalently bound within the functionalized silane host 104, forming a host-guest complex. The composition 100 has the ability of targeted drug delivery. After administered via a certain route, the porous silicon nanoparticles contained in the composition act as a carrier for the active agent and aid in its delivery to targeted tissues in the body, thereby reducing off-target toxicity. On account of the host-guest complex, the active agent non-covalently bound within the host is released sustainably from the host cavity, achieving a prolonged therapeutic effect.

Figure 2:
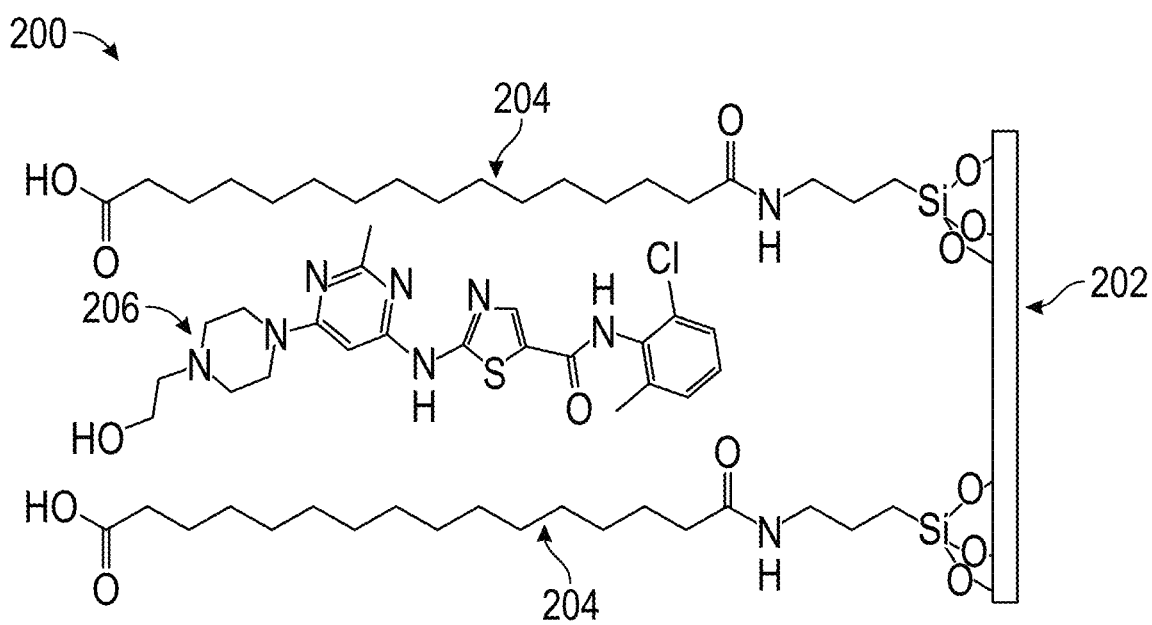
FIG. 2 is a Lewis structure or molecular representation of an embodiment of a composition including an embodiment of host molecular structure and dasatinib as an embodiment of an active agent.

Referring to FIG. 2, an embodiment of the composition disclosed herein 200 is shown that includes a porous silicon nanoparticle having a pore surface 202 and a functionalized silane host 204 adhered to surface 202 of a pore of the porous particle. As shown in FIG. 2, the composition 200 also includes dasatinib 206 as a guest which is non-covalently bound within the functionalized silane host 204, forming a host-guest complex.

Figure 3:
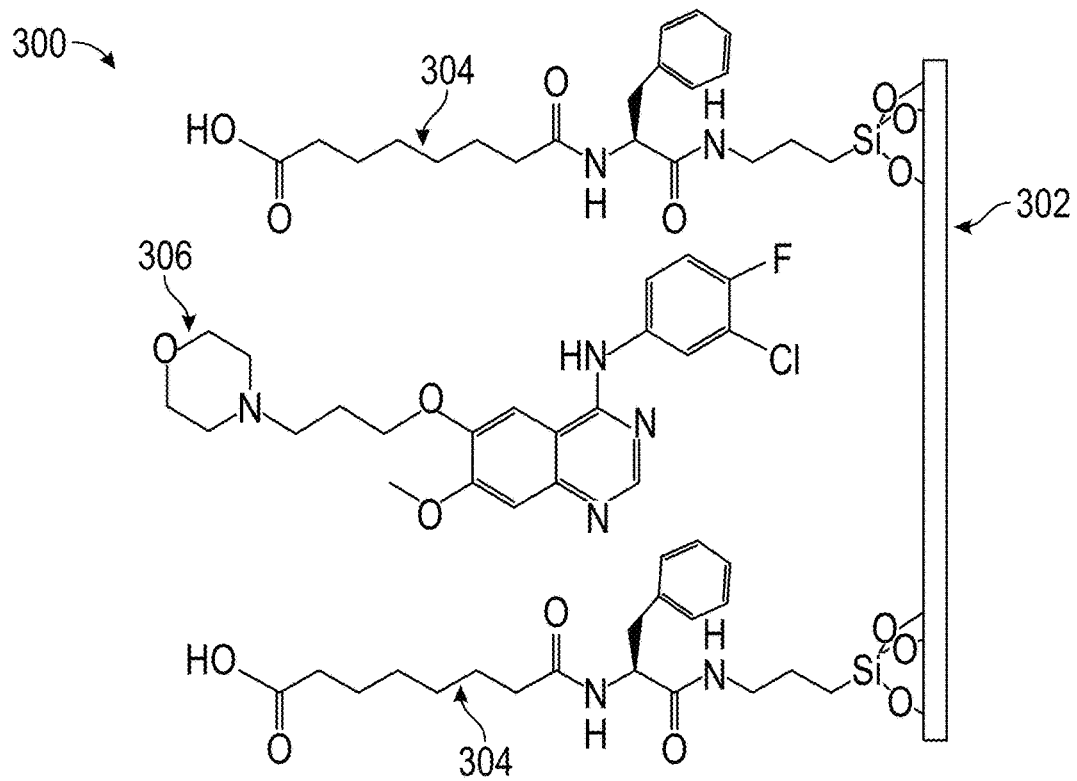
FIG. 3 is a Lewis structure or molecular representation of an embodiment of a composition including an embodiment of host molecular structure and gefitinib as an embodiment of an active agent.

Referring to FIG. 3, there is shown an embodiment of the composition 300 that can be used to deliver the active agent gefitinib to a cell in a target tissue of a subject in need thereof. In this embodiment, the composition 300 includes a porous silicon nanoparticle having a pore surface 302 and a functionalized silane host 304 adhered to surface 302 of a pore of the porous particle. As illustrated in FIG. 3, the composition 300 also includes gefitinib 306 as a guest which is non-covalently bound within the functionalized silane host 304, forming a host-guest complex.

Figure 4:
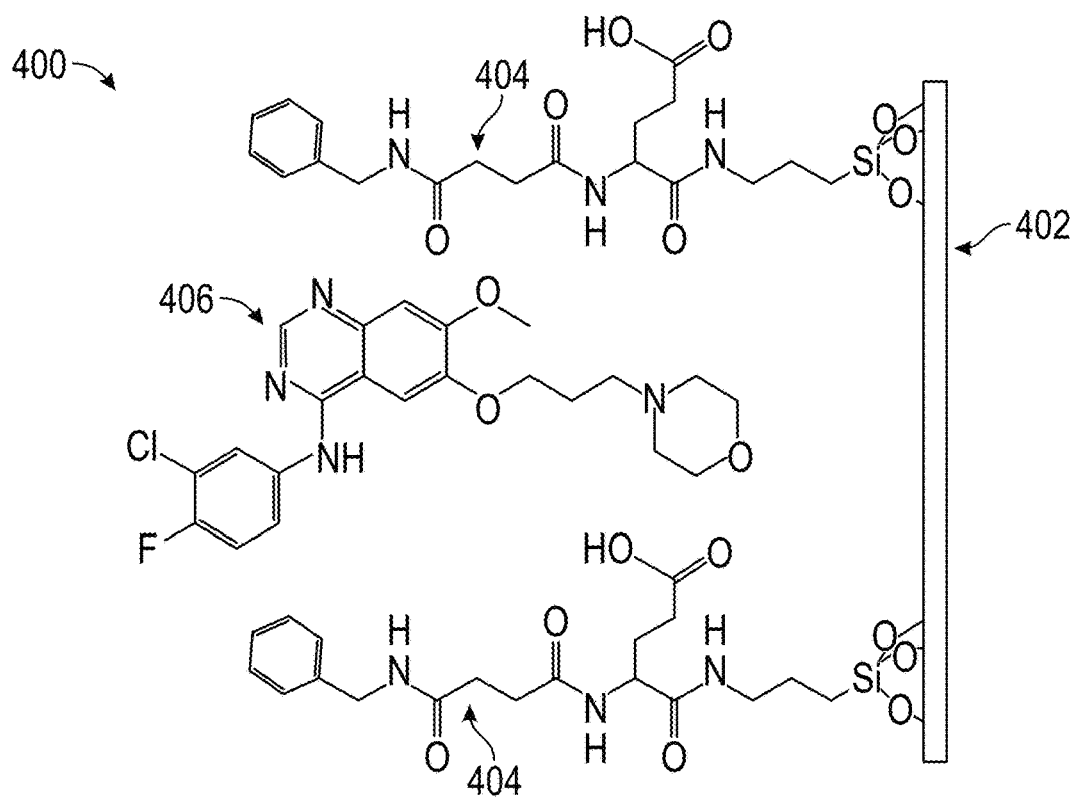
FIG. 4 is a Lewis structure or molecular representation of an embodiment of a composition including an embodiment of host molecular structure and gefitinib as an embodiment of an active agent.

Referring to FIG. 4, there is shown an embodiment of the composition 400. In this embodiment, the composition 400 includes a porous silicon nanoparticle having a pore surface 402 and a host-guest complex comprising a functionalized silane 404 as a host and gefitinib 406 as a guest, wherein the host is bound within the guest. As shown in FIG. 4, the functionalized silane host 404 is adhered to surface 402 of a pore of the porous particle.

Figure 5:
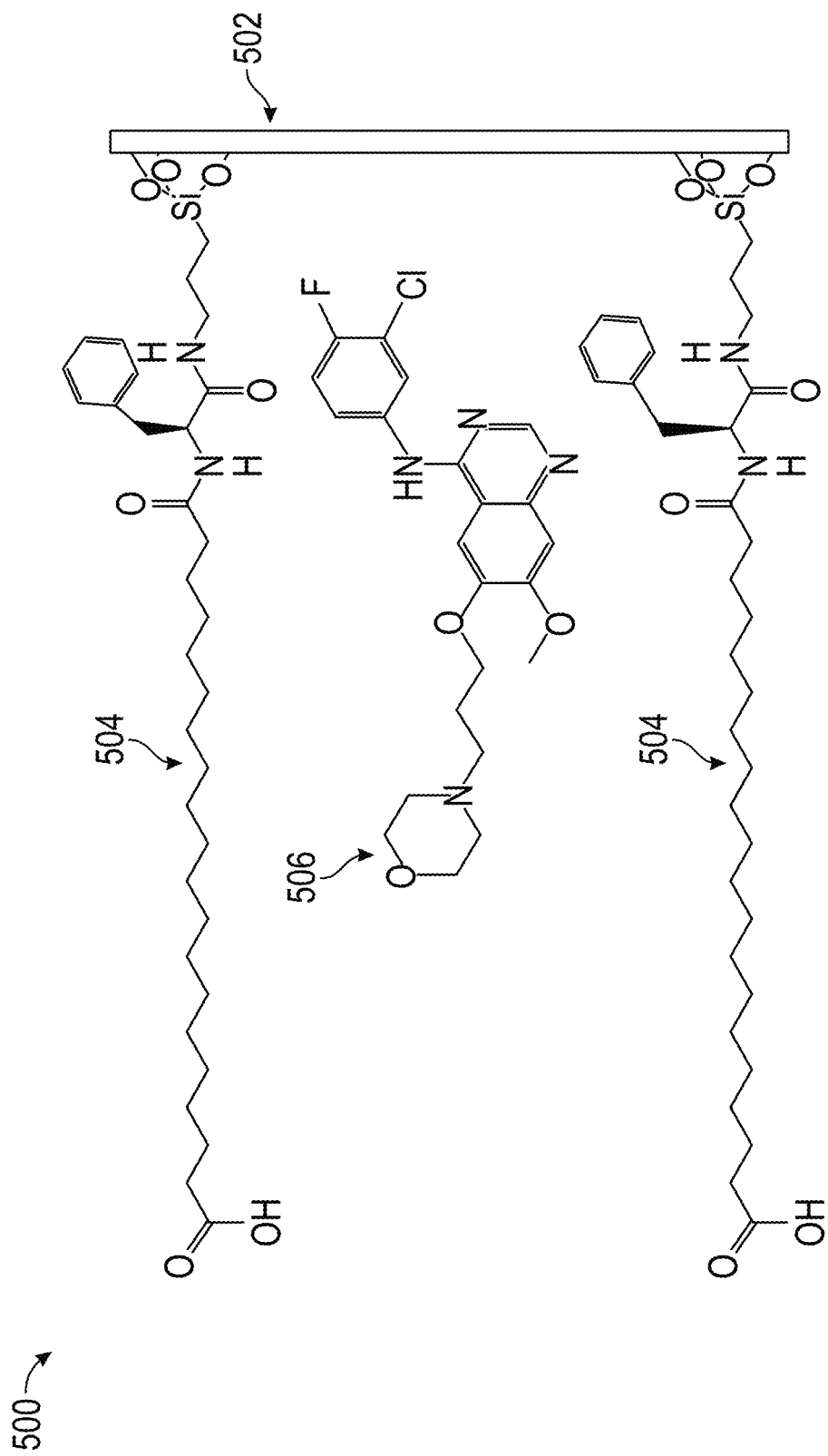
FIG. 5 is a Lewis structure or molecular representation of an embodiment of a composition including an embodiment of host molecular structure and gefitinib as an embodiment of an active agent.

Referring to FIG. 5, an embodiment of the composition disclosed herein 500 is shown that includes a porous silicon nanoparticle having a pore surface 502 and a host-guest complex comprising a functionalized silane host 504 and a gefitinib guest 506. The functionalized silane host 504 is adhered to surface 502 of a pore of the porous particle, as shown in FIG. 5.

Figure 6:
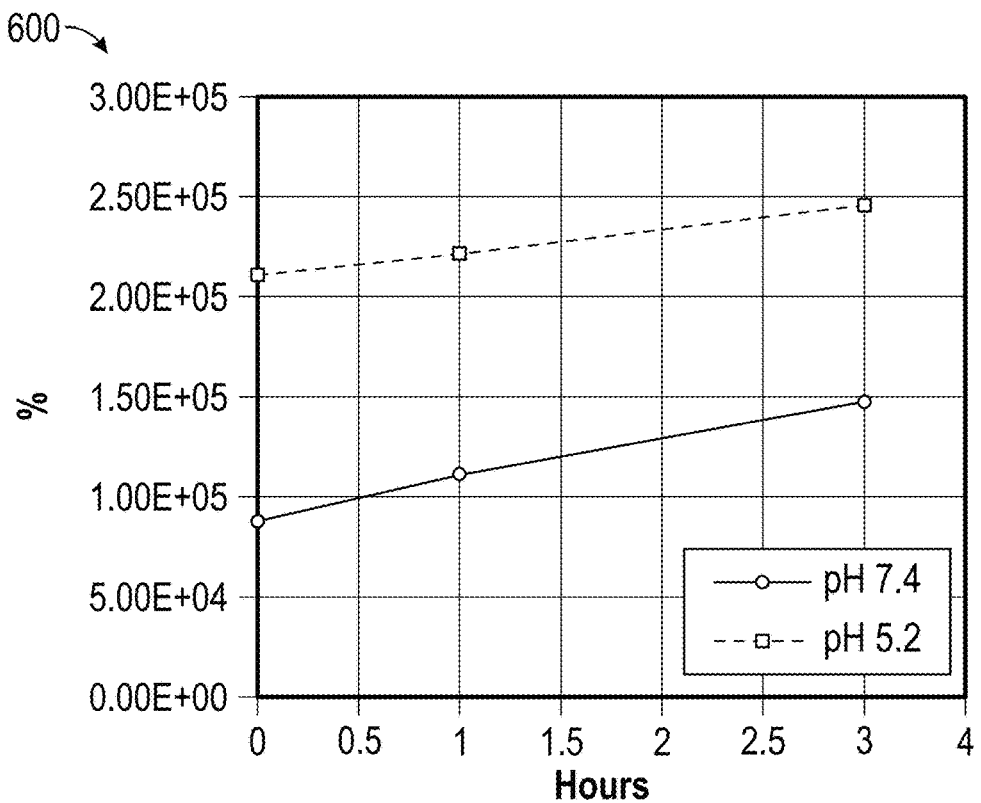
FIG. 6 is a graph showing release kinetics of dasatinib from an embodiment of a composition according to the present disclosure in buffer solution at pH 7.4 and pH 5.2.

FIG. 6 shows release kinetics of dasatinib from a composition according to the present disclosure in dimethyl sulfoxide (DMSO) solution at pH 7.4 and pH 5.2, as a function of time.

Figure 7:
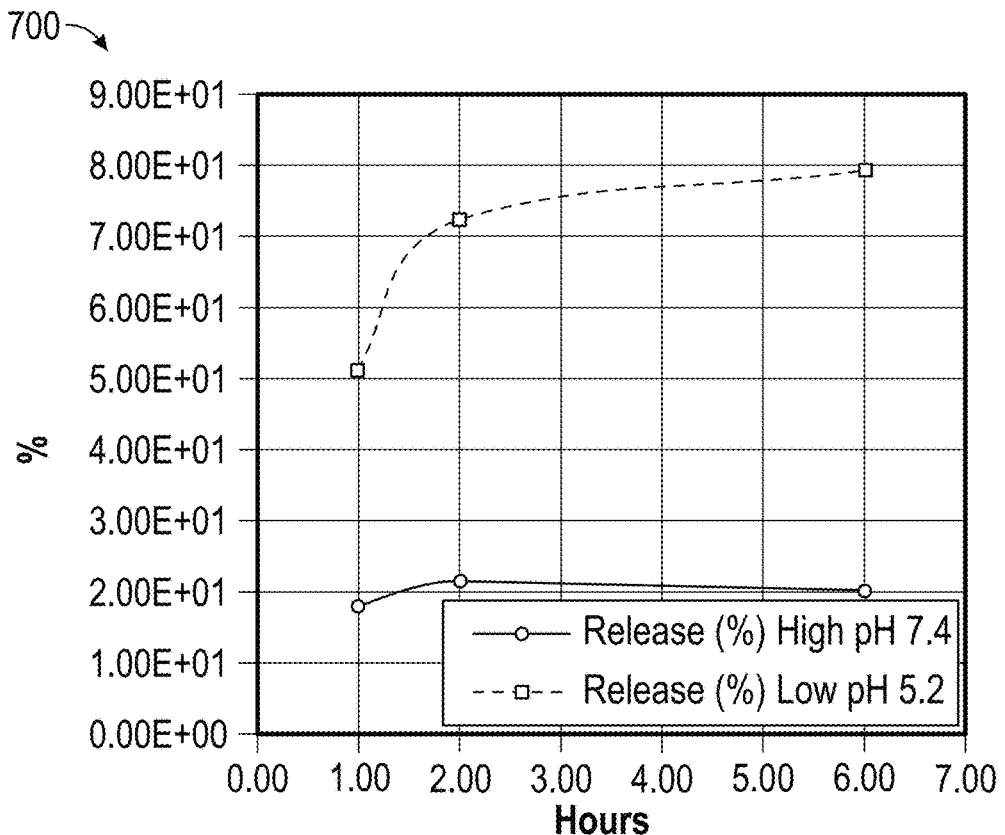
FIG. 7 is a graph showing release kinetics of dasatinib from an embodiment of a composition according to the present disclosure in buffer solution at pH 7.4 and pH 5.2.

FIG. 7 shows release kinetics of dasatinib from a composition according to the present disclosure in water at pH 7.4 and pH 5.2, as a function of time.

Figure 8:
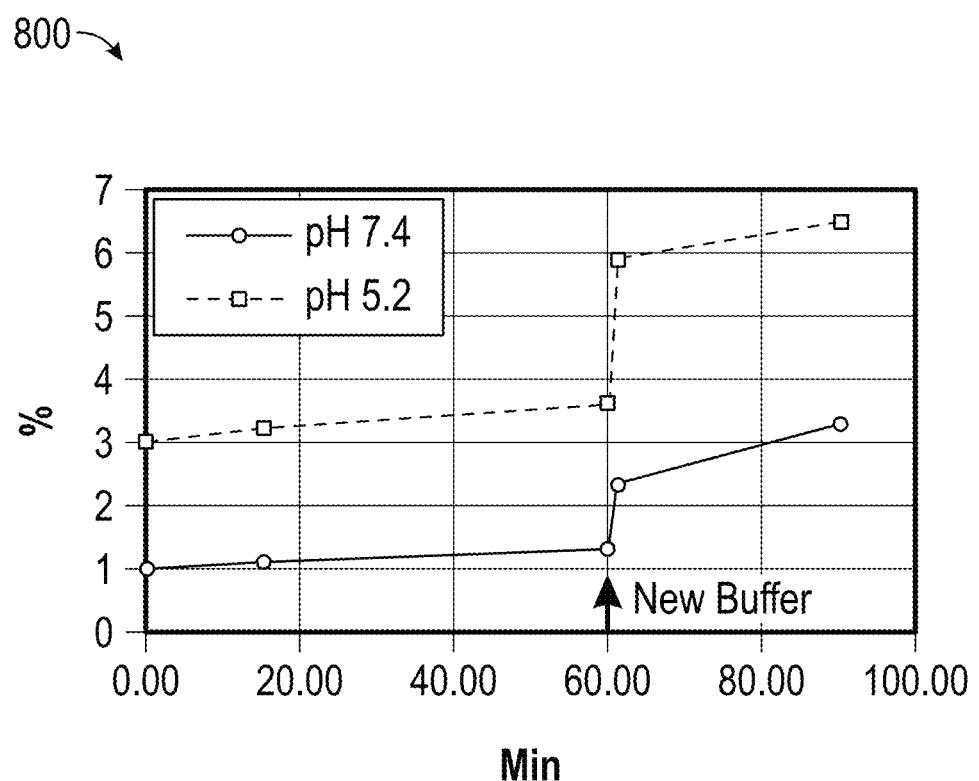
FIG. 8 is a graph showing release kinetics of gefitinib from an embodiment of a composition according to the present disclosure in buffer solution at pH 7.4 and pH 5.2.
Figure 9:
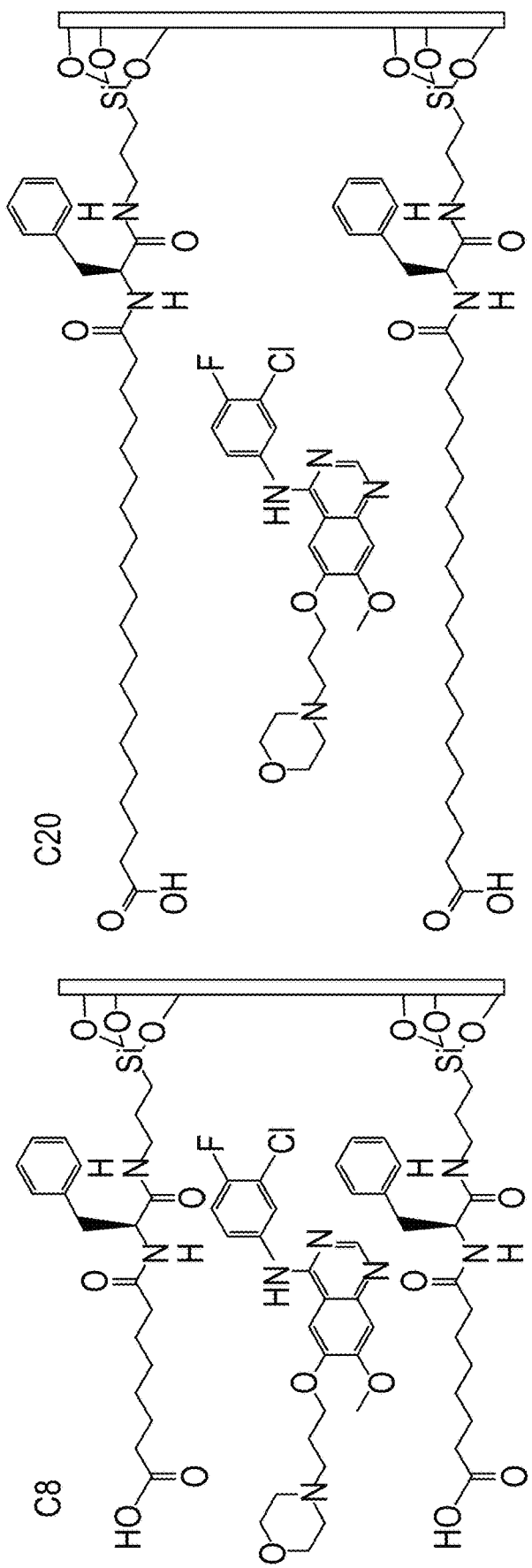
FIG. 9 is a Lewis structure or molecular representation of an embodiment of a composition including an embodiment of host molecular structure and gefitinib as an embodiment of an active agent.

FIG. 8 shows release kinetics of gefitinib from a composition according to the present disclosure in phosphate buffer solution at pH 7.4 and pH 5.2, as a function of time.

The present disclosure provides compositions and methods for delivering therapeutic agents to particular tissues or cells in a subject. The present disclosure also provides methods for synthesizing compositions capable of delivering therapeutic agents to particular tissues or cells in a subject.

In some embodiments, the present disclosure provides a composition for delivery of an active agent to a cell in a target tissue of a subject in need thereof, which comprises: an active agent; and a porous particle, wherein the porous particle comprises a plurality of microscale reservoirs and a host molecular structure is adhered to a surface of the porous particle. The host molecular structure has a structure of Formula 1, wherein:

Formula 1

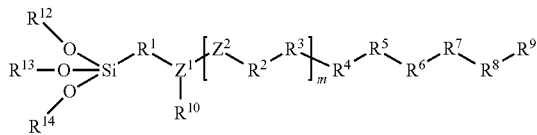

$R^1$ is —($C_1$-$C_6$)alkylene, or —H;
$Z^1$ is —(N—)—, —H, or none;
$Z^2$ is —(C(=O))—, —$SO_2$—, or none;
$R^2$ is —(C(—H)—$R^{11}$)—, —($C_1$-$C_3$)alkylene, —(C(—H)—(($C_1$-$C_6$)alkylene-(C(=O)(—O⁻X))))—, —(C(—H)(—($C_1$-$C_6$)alkylene-$Ar^1$))—, —O—, —H, or none;
$R^3$ is —($CH_2$)—, —(N(—H))—, —H, or none;
$R^4$ is —($CH_2$)—, —(C(=O))—, —H, or none;
$R^5$ is —($C_1$-$C_{20}$)alkylene, —($C_1$-$C_3$)alkylene-$Ar^2$, —O—, —H, or none;
$R^6$ is —($CH_2$)—, —H, or none;
$R^7$ is —($CH_2$)—, —(C(=O))—, —H, or none;
$R^8$ is —($CH_2$)—, —(N(—H))—, —H, or none;

$R^9$ is —($C_1$-$C_3$)alkylene-$Ar^2$, —(C(=O)(—O⁻X)), ($C_1$-$C_{20}$)alkylene-(C(=O)(—O⁻X)), —($C_1$-$C_2$O)alkyl, —H, or none;
$R^{10}$ is —($C_1$-$C_6$)alkyl, or —H;
$R^{11}$ is side chain of amino acid such as methyl group (—$CH_3$), guanidino group (—($CH_2$)$_3$—NH—C(=NH)—$NH_2$), amide group (—$CH_2$—$CONH_2$), (—$CH_2$—$CH_2$—$CONH_2$), carboxyl group (—$CH_2$—COOH), (—$CH_2$—$CH_2$—COOH), thiol group (—$CH_2$—SH), amide group (—$CH_2$—$CH_2$—$CONH_2$), carboxyl group (—$CH_2$—$CH_2$—COOH), hydrogen atom (—H), imidazole group (—$CH_2$—$C_3H_3N_2$), sec-butyl group (—CH($CH_3$)—$CH_2$—$CH_3$), isobutyl group (—$CH_2$—CH($CH_3$)$_2$), amino group (—($CH_2$)$_4$—$NH_2$), (—($CH_2$)$_3$—$NH_2$), thioether group (—$CH_2$—$CH_2$—S—$CH_3$), hydroxymethyl group (—$CH_2$—OH), hydroxyethyl group (—CH(OH)—$CH_3$), hydroxyphenyl group (—$CH_2$-$C_6H_4$—OH), isopropyl group (—CH($CH_3$)$_2$), or their derivative;
m is 0~150;
provided that if m>2, then $Ar^1$ or $R^{11}$ can be chosen independently;
$Ar^1$ is a substituted phenyl, an unsubstituted phenyl, a substituted indole, or an unsubstituted indole;
$Ar^2$ is a substituted phenyl, an unsubstituted phenyl, a substituted naphthyl, an unsubstituted naphthyl, a substituted indole, or an unsubstituted indole; and
X is H⁺, Na⁺, Ca⁺, or K⁺, and $R^{12}$, $R^{13}$, and $R^{14}$, each independently, represents the surface of the porous particle or an adjacent silane.

In some embodiments, the host molecular structure has a structure of Formula 1, wherein:
$Z^1$ is —(N—)—;
$Z^2$ is —(C(=O))—;
$R^2$ is —(C(—H)(—($C_1$-$C_6$)alkylene-$Ar^1$)) and $Ar^1$ is an unsubstituted phenyl;
$R^3$ is —(N(—H))—;
$R^4$ is —(C(=O))—;
$R^9$ is —($C_1$-$C_{20}$)alkylene-(C(=O)(—O⁻X)); and
$R^{10}$ is —H.

In some embodiments, the host molecular structure has a structure of Formula 1, wherein:
$Z^1$ is —(N—)—;
$Z^2$ is —(C(=O))—;
$R^2$ is —(C(—H)—(($C_1$-$C_6$)alkylene-(C(=O)(—O⁻X))))—;
$R^3$ is —(N(—H))—;
$R^4$ is —(C(=O))—;
$R^7$ is —(C(=O))—;
$R^9$ is —($C_1$-$C_3$)alkylene-$Ar^2$ and $Ar^2$ is an unsubstituted phenyl; and
$R^{10}$ is —H.

In some embodiments, the host molecular structure has a structure of Formula 1, wherein:
$Z^1$ is —(N—)—;
$Z^2$ is —(C(=O))—;
$R^9$ is —($C_1$-$C_3$)alkylene-$Ar^2$, —(C(=O)(—O⁻X)), ($C_1$-$C_{20}$)alkylene-(C(=O)(—O⁻X)), or ($C_1$-$C_{20}$)alkyl; and
$R^{10}$ is —H.

In some embodiments, the host molecular structure has a structure of Formula 2, Formula 3, Formula 4, or Formula 5, or mixture thereof:

Formula 2

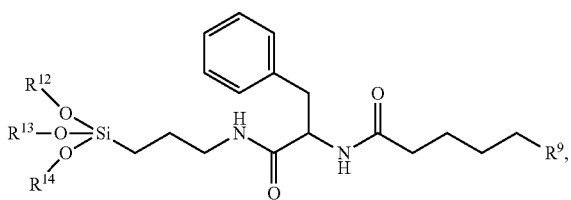

wherein R$^9$ is —(C$_1$-C$_{20}$)alkylene-(C(=O)(—O$^-$X));

Formula 3

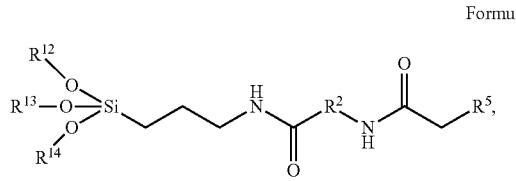

wherein R$^2$ is —(C(—H)—((C$_1$-C$_6$)alkylene-(C(=O)(—O$^-$X)))) and R$^5$ is —(C$_1$-C$_3$)alkylene-Ar$^2$;

Formula 4

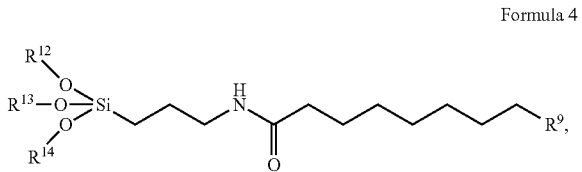

wherein R$^9$ is —(C$_1$-C$_{20}$)alkyl; and

Formula 5

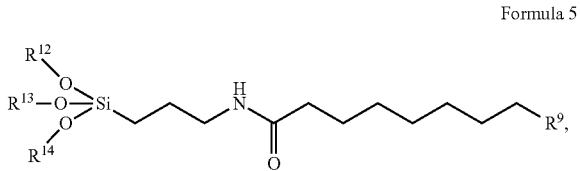

wherein R$^9$ is —(C$_1$-C$_{20}$)alkylene-(C(=O)(—O$^-$X));
wherein R$^{12}$, R$^{13}$, and R$^{14}$, each independently, represents the surface of the porous particle or an adjacent silane.

In some embodiments, the porous particle is a micro or a nano particle. In some embodiments, the porous particle is biocompatible and degradable. In some embodiments, the plurality of microscale reservoirs of the porous particle has a size ranging from about 0.3 μm to about 4 μm, including about 0.4 μm to about 4 μm, about 0.5 μm to about 4 μm, about 0.6 μm to about 4 μm, about 0.7 μm to about 4 μm, about 0.8 μm to about 4 μm, about 0.9 μm to about 4 m, about 1 μm to about 4 μm, about 1.5 μm to about 4 μm, about 2.0 μm to about 4 μm, about 2.5 μm to about 4 μm, about 3.0 μm to about 4 μm, about 3.5 μm to about 4 μm, about 0.3 μm to about 3.5 μm, about 0.3 μm to about 3.0 μm, about 0.3 μm to about 2.5 μm, about 0.3 μm to about 2.0 μm, about 0.3 μm to about 1.5 μm, about 0.3 μm to about 1.0 μm, about 0.3 μm to about 0.8 μm, about 0.3 μm to about 0.5 μm, about 1 μm to about 3 μm, about 1.5 μm to about 3 μm, and about 2 μm to about 4 μm. A benefit of particle size can be controlling or selecting which type of cells or tissues the particles can enter or selectively enter.

In some embodiments, the porous particle has a shape selected from the group consisting of discoidal, spheroid, non-spheroid, oblate spheroid, and combinations thereof. A benefit of particle shape can be controlling or selecting which type of cells or tissues the particles can enter or selectively enter. In some embodiments, the porous particle includes a porous oxide material or a porous etched material. In some embodiments, the porous particle is able to overcome at least one biological barrier.

In some embodiments, the porous particle includes a porous oxide material selected from the group consisting of porous silica, porous aluminum oxide, porous titanium oxide, porous iron oxide, and combinations thereof. In some embodiments, the porous particle includes a porous etched material selected from the group consisting of porous silicon, porous silica, porous germanium, porous GaAs, porous InP, porous SiC, porous Si$_x$Ge$_{1-x}$, porous GaP, porous GaN, and combinations thereof. A benefit of a porous material or porous oxide material can be the compatibility of these materials with known microfabrication techniques, such as patterning and etching.

In some embodiments, the active agent includes a kinase inhibitor. In some embodiments, the surface of the porous particle includes an interior surface of a pore of the porous particle. In some embodiments, the active agent is retained for a longer duration at a retention pH by a porous particle having the molecular host structure than a porous particle or a porous particle that excludes the molecular host structure. In some embodiments, the active agent forms a non-covalent complex with the molecular host structure.

In some embodiments, the active agent includes a kinase inhibitor selected from the group consisting of:
Abemaciclib (N-[5-[(4-Ethyl-1-piperazinyl)methyl]-2-pyridinyl]-5-fluoro-4-[4-fluoro-2-methyl-1-(1-methylethyl)-1H-benzimidazol-6-yl]-2-pyrimidinamine);
Abrocitinib (N-[3-[methyl(7H-pyrrolo[2,3-d]pyrimidin-4-yl)amino]cyclobutyl]propane-1-sulfonamide);
Acalabrutinib (4-{8-Amino-3-[(2S)-1-(2-butynoyl)-2-pyrrolidinyl]imidazo[1,5-a]pyrazin-1-yl}-N-(2-pyridinyl)benzamide);
Afatinib (N-[4-[(3-Chloro-4-fluorophenyl)amino]-7-[[(3S)-tetrahydro-3-furanyl]oxy]-6-quinazolinyl]-4(dimethylamino)-2-butenamide);
Alectinib (9-Ethyl-6,6-dimethyl-8-[4-(morpholin-4-yl)piperidin-1-yl]-11-oxo-6,11-dihydro-5H-benzo[b]carbazole-3-carbonitrile);
Almonertinib (N-[5-[[4-(1-cyclopropylindol-3-yl)pyrimidin-2-yl]amino]-2-[2-(dimethylamino)ethyl-methylamino]-4-methoxyphenyl]prop-2-enamide);
Alpelisib ((2S)-1-N-[4-Methyl-5-[2-(1,1,1-trifluoro-2-methylpropan-2-yl)pyridin-4-yl]-1,3-thiazol-2-yl]pyrrolidine-1,2-dicarboxamide);
Amivantamab (antibody, CAS Number 2171511-58-1, UNII OJSR7ZONB6, Unique Ingredient Identifier);
Apatinib (N-(4-(1-Cyanocyclopentyl)phenyl)-2-((pyridin-4-ylmethyl)amino)nicotinamide);
Asciminib (N-4-[chloro(difluoro)methoxy]phenyl]-6-[(3R)-3-hydroxypyrrolidin-1-yl]-5-(1H-pyrazol-5-yl)pyridine-3-carboxamide);
Avapritinib ((1S)-1-(4-fluorophenyl)-1-(2-{4-[6-(1-methyl-1H-pyrazol4-yl)pyrrolo[2,1-f][1,2,4]triazin-4-yl]piperazin-1-yl}pyrimidin5-yl)ethan-1-amine);
Axitinib (N-Methyl-2-[[3-[(E)-2-pyridin-2-ylethenyl]-1H-indazol-6-yl]sulfanyl]benzamide);
Baricitinib (2-[1-Ethylsulfonyl-3-[4-(7H-pyrrolo[2,3-d]pyrimidin-4-yl)pyrazol-1-yl]azetidin-3-yl]acetonitrile);

Binimetinib (5-((4-bromo-2-fluorophenyl)amino)-4-fluoro-N-(2-hydroxyethoxy)-1-methyl-1H-benzo[d]imidazole-6-carboxamide);

Bosutinib (4-[(2,4-dichloro-5-methoxyphenyl)amino]-6-methoxy-7-[3-(4-methylpiperazin-1-yl)propoxy]quinoline-3-carbonitrile);

Brigatinib (5-Chloro-2-N-{4-[4-(dimethylamino)piperidin-1-yl]-2-methoxyphenyl}-4-N-[2-(dimethylphosphoryl)phenyl]pyrimidine-2,4-diamine);

Cabozantinib (N-(4-((6,7-Dimethoxyquinolin-4-yl)oxy)phenyl)-N'-(4-fluorophenyl)cyclopropane-1,1-dicarboxamide);

Capivasertib (4-Amino-N-[(1S)-1-(4-chlorophenyl)-3-hydroxypropyl]-1-(7H-pyrrolo[2,3-d]pyrimidin-4-yl)piperidine-4-carboxamide);

Capmatinib (2-Fluoro-N-methyl-4-[7-(quinolin-6-ylmethyl)imidazo[1,2-b][1,2,4]triazin-2-yl]benzamide);

Catequentinib (1-[[4-[(4-fluoro-2-methyl-1H-indol-5-yl)oxy]-6-methoxyquinolin-7-yl]oxymethyl]cyclopropan-1-amine);

Ceritinib (5-Chloro-N2-{5-methyl-4-(piperidin-4-yl)-2-[(propan-2-yl)oxy]phenyl}-N4-[2-(propane-2-sulfonyl)phenyl]pyrimidine-2,4-diamine);

Cetuximab (antibody, CAS Number 205923-56-4, UNII PQXOD8J21J);

Cobimetinib ((S)-[3,4-Difluoro-2-(2-fluoro-4-iodophenylamino)phenyl][3-hydroxy-3-(piperidin-2-yl)azetidin-1-yl]methanone);

Copanlisib (2-Amino-N-[7-methoxy-8-(3-morpholin-4-ylpropoxy)-2,3-dihydroimidaz[1,2-c]quinazolin-5-yl]pyrimidine-5-carboxamide);

Crizotinib (3-[(1R)-1-(2,6-dichloro-3-fluorophenyl)ethoxy]-5-(1-piperidin-4-ylpyrazol-4-yl)pyridin-2-amine);

Dabrafenib (N-{3-[5-(2-aminopyrimidin-4-yl)-2-tert-butyl-1,3-thiazol-4-yl]-2-fluorophenyl}-2,6-difluorobenzenesulfonamide);

Dacomitinib ((2E)-N-{4-[(3-Chloro-4-fluorophenyl)amino]-7-methoxy-6-quinazolinyl}-4-(1-piperidinyl)-2-butenamide);

Dasatinib (N-(2-chloro-6-methylphenyl)-2-[[6-[4-(2-hydroxyethyl)-1-piperazinyl]-2-methyl-4-pyrimidinyl]amino]-5-thiazole carboxamide monohydrate);

Defactinib (N-methyl-4-[[4-[[3-[methyl(methylsulfonyl)amino]pyrazin-2-yl]methylamino]-5-(trifluoromethyl)pyrimidin-2-yl]amino]benzamide);

Delgocitinib (3-[(3S,4R)-3-Methyl-7-(7H-pyrrolo[2,3-d]pyrimidin-4-yl)-1,7-diazaspiro[3.4]octan-1-yl]-3-oxopropanenitrile);

Deucravacitinib (6-(cyclopropanecarboxamido)-4-((2-methoxy-3-(1-methyl-1,2,4-triazol-3-yl)phenyl)amino)-N-(trideuteromethyl)pyridazine-3-carboxamide);

Duvelisib (8-Chloro-2-phenyl-3-[(1S)-1-(3H-purin-6-ylamino)ethyl]-1(2H)-isoquinolinone);

Encorafenib (Methyl [(2S)-1-{[4-(3-{5-chloro-2-fluoro-3-[(methylsulfonyl)amino]phenyl}-1-isopropyl-1H-pyrazol-4-yl)-2-pyrimidinyl]amino}-2-propanyl]carbamate);

Entrectinib (N-[5-(3,5-Difluorobenzyl)-1H-indazol-3-yl]-4-(4-methyl-1-piperazinyl)-2-(tetrahydro-2H-pyran-4-ylamino)benzamide);

Erdafitinib (N'-(3,5-dimethoxyphenyl)-N'-[3-(1-methylpyrazol-4-yl)quinoxalin-6-yl]-N-propan-2-ylethane-1,2-diamine);

Erlotinib (N-(3-ethynylphenyl)-6,7-bis(2-methoxyethoxy)quinazolin-4-amine);

Everolimus (Dihydroxy-12-[(2R)-1-[(1S,3R,4R)-4-(2-hydroxyethoxy)-3-methoxycyclohexyl]propan-2-yl]-19,30-dimethoxy-15,17,21,23,29,35-hexamethyl-11,36-dioxa-4-azatricyclo[30.3.1.0 hexatriaconta-16,24,26,28-tetraene-2,3,10,14,20-pentone);

Fasudil (5-(1,4-Diazepane-1-sulfonyl)isoquinoline);

Fedratinib (N-tert-Butyl-3-{5-methyl-2-[4-(2-pyrrolidin-1-yl-ethoxy)-phenylamino]-pyrimidin-4-ylamino}-benzenesulfonamide);

Filgotinib (N-[5-[4-[(1,1-Dioxo-1,4-thiazinan-4-yl)methyl]phenyl]-[1,2,4]triazolo[1,5-a]pyridin-2-yl]cyclopropanecarboxamide);

Flumatinib (4-[(4-Methyl-1-piperazinyl)methyl]-N-(6-methyl-5-{[4-(3-pyridinyl)-2-pyrimidinyl]amino}-3-pyridinyl)-3-(trifluoromethyl)benzamide);

Fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl]methyl dihydrogen phosphate);

Fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl]methyl dihydrogen phosphate);

Fruquintinib (6-[(6,7-dimethoxyquinazolin-4-yl)oxy]-N,2-dimethyl-1-benzofuran-3-carboxamide);

Furmonertinib; N-[2-[2-(dimethylamino)ethyl-methylamino]-5-[[4-(1-methylindol-3-yl)pyrimidin-2-yl]amino]-6-(2,2,2-trifluoroethoxy)pyridin-3-yl]prop-2-enamide;

Futibatinib (1-[(3S)-3-[4-amino-3-[2-(3,5-dimethoxyphenyl)ethynyl]pyrazolo[3,4-d]pyrimidin-1-yl]pyrrolidin-1-yl]prop-2-en-1-one);

Gefitinib (N-(3-chloro-4-fluoro-phenyl)-7-methoxy-6-(3-morpholin-4-ylpropoxy)quinazolin-4-amine);

Gilteritinib (6-Ethyl-3-[3-methoxy-4-[4-(4-methylpiperazin-1-yl)piperidin-1-yl]anilino]-5-(oxan-4-ylamino)pyrazine-2-carboxamide);

Ibrutinib (1-[(3R)-3-[4-Amino-3-(4-phenoxyphenyl)-1H-pyrazolo[3,4-d]pyrimidin-1-yl]piperidin-1-yl]prop-2-en-1-one);

Icotinib N-3-(Ethylphenul)-7,8,10,11,12,14-hexahydro[1,4,7,10]tetraoxacyclododecino[2,3-g]quinazolin-4-amine;

Idelalisib (5-Fluoro-3-phenyl-2-[(1S)-1-(7H-purin-6-ylamino)propyl]-4(3H)-quinazolinone);

Imatinib (4-[(4-methylpiperazin-1-yl)methyl]-N-(4-methyl-3-{[4-(pyridin-3-yl)pyrimidin-2-yl]amino}phenyl)benzamide);

Infigratinib (3-(2,6-Dichlor-3,5-dimethoxyphenyl)-1-(6-{[4-(4-ethyl-1-piperazinyl)phenyl]amino}-4-pyrimidinyl)-1-methylurea);

Ivosidenib ((2S)-N-{(1S)-1-(2-chlorophenyl)-2-[(3,3-difluorocyclobutyl)amino]-2-oxoethyl}-1-(4-cyanopyridin2-yl)-N-(5-fluoropyridin-3-yl)-5-oxopyrrolidine2-carboxamide);

Lapatinib (N-[3-Chloro-4-[(3-fluorophenyl)methoxy]phenyl]-6-[5-[(2-methylsulfonylethylamino)methyl]-2-furyl]quinazolin-4-amine);

Larotrectinib ((3S)-N-{5-[(2R)-2-(2,5-difluorophenyl)pyrrolidin-1-yl]pyrazolo[1,5-a]pyrimidin-3-yl}-3-hydroxypyrrolidine-1-carboxamide);

Lazertinib (N-[5-[[4-[4-[(dimethylamino)methyl]-3-phenylpyrazol-1-yl]pyrimidin-2-yl]amino]-4-methoxy-2-morpholin-4-ylphenyl]prop-2-enamide);

Leniolisib (1-[(3S)-3-({6-[6-Methoxy-5-(trifluoromethyl)-3-pyridinyl]-5,6,7,8-tetrahydropyrido[4,3-d]pyrimidin-4-yl}amino)-1-pyrrolidinyl]-1-propanone);

Lenvatinib (4-[3-Chloro-4-(cyclopropylcarbamoylamino)phenoxy]-7-methoxy-quinoline-6-carboxamide);

Lorlatinib ((10R)-7-Amino-12-fluoro-2,10,16-trimethyl-15-oxo-10,15,16,17-tetrahydro-2H-4,8-methenopyrazolo[4,3-h][2,5,11]benzoxadiazacyclotetradecine-3-carbonitrile);

Margetuximab (antibody, CAS Number 1350624-75-7, UNII K911R84KEW);

Midostaurin ((9S,10R,11R,13R)-2,3,10,11,12,13-Hexahydro-10-methoxy-9-methyl-11-(methylamino)-9,13-epoxy-1H,9H-diindolo[1,2,3-gh:3',2',1'-lm]pyrrolo[3,4 j][1,7]benzodiamzonine-1-one);

Mobocertinib (Propan-2-yl 2-(4-{[2-(dimethylamino)ethyl]methylamino}-2-methoxy-5-(prop-2-enamido)anilino)-4-(1-methyl-1H-indol-3-yl)pyrimidine-5-carboxylate);

Necitumumab (antibody, CAS Number 906805-06-9, UNII 2BT4C47RUI);

Neratinib ((2E)-N-[4-[[3-Chloro-4-[(pyridin-2-yl)methoxy]phenyl]amino]-3-cyano-7-ethoxyquinolin-6-yl]-4-(dimethylamino)but-2-enamide);

Netarsudil ([4-[(2S)-3-Amino-1-(isoquinolin-6-ylamino)-1-oxopropan-2-yl]phenyl]methyl 2,4-dimethylbenzoate);

Nilotinib (4-methyl-N-[3-(4-methyl-1H-imidazol-1-yl)-5-(trifluoromethyl)phenyl]-3-[(4-pyridin-3-ylpyrimidin-2-yl) amino]benzamide);

Nimotuzumab (antibody, CAS Number 780758-10-3, UNII 6NS400BXKH);

Nintedanib (Methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate);

Olaratumab (antibody, CAS Number 1024603-93-7, UNII TT6HN20MVF);

Olmutinib (N-{3-[(2-{[4-(4-Methyl-1-piperazinyl)phenyl]amino}thieno[3,2-d]pyrimidin-4-yl)oxy]phenyl}acrylamide);

Orelabrutinib (2-(4-Phenoxyphenyl)-6-(1-prop-2-enoylpiperidin-4-yl)pyridine-3-carboxamide);

Osimertinib (N-(2-{[2-(dimethylamino)ethyl](methyl)amino}-4-methoxy-5-{[4-(1-methyl-1H-indol-3-yl)pyrimidin-2-yl]amino}phenyl)prop-2-enamide);

Pacritinib ((16E)-11-[2-(1-Pyrrolidinyl)ethoxy]-14,19-dioxa-5,7,26-triazatetracyclo[19.3.1.12,6.18,12]heptacosa-1(25),2(26),3,5,8,10,12(27),16,21,23-decaene), Palbociclib (6-Acetyl-8-cyclopentyl-5-methyl-2-{[5-(1-piperazinyl)-2-pyridinyl]amino}pyrido[2,3-d]pyrimidin-7(8H)-one);

Panitumumab (antibody, CAS Number 339177-26-3, UNII 6A901E312A);

Paxalisib (5-(4-morpholinyl)-8-(1H-pyrazol-4-yl)-4-(trifluoromethyl)-2H-pyrido[4,3-b]pyridin-3-one);

Pazopanib (5-({4-[(2,3-Dimethyl-2H-indazol-6-yl)methylamino]pyrimidin-2-yl}amino)-2-methylbenzenesulfonamide);

Peficitinib (4-{[(1R,2s,3S,5s,7s)-5-Hydroxyadamantan-2-yl]amino}-1H-pyrrolo[2,3-b]pyridin-5-carboxamide;

Pemigatinib (3-(2,6-difluoro-3,5-dimethoxyphenyl)-1-ethyl-8-[(morpholin4-yl)methyl]-1,3,4,7-tetrahydro-2H-pyrrolo[3',2':5,6]pyrido[4,3-d]pyrimidin-2-one);

Pertuzumab (antibody, CAS Number 380610-27-5, UNII K16AIQ8CTM);

Pexidartinib (5-[(5-Chloro-1H-pyrrolo[2,3-b]pyridin-3-yl)methyl]-N-{[6-(trifluoromethyl)-3-pyridinyl]methyl}-2-pyridinamine);

Pirtobrutinib (5-amino-3-[4-[[(5-fluoro-2-methoxybenzoyl)amino]methyl]phenyl]-1-[(2S)-1,1,1-trifluoropropan-2-yl]pyrazole-4-carboxamide);

Ponatinib (3-(2-Imidazo[1,2-b]pyridazin-3-ylethynyl)-4-methyl-N-[4-[(4-methylpiperazin-1-yl)methyl]-3-(trifluoromethyl)phenyl]benzamide);

Pralsetinib (N-[(1S)-1-[6-(4-fluoropyrazol-1-yl)pyridin-3-yl]ethyl]-1-methoxy-4-[4-methyl-6-[(5-methyl-1H-pyrazol-3-yl)amino]pyrimidin-2-yl]cyclohexane-1-carboxamide);

Pyrotinib ((2E)-N-(4-{[3-Chloro-4-(2-pyridinylmethoxy)phenyl]amino}-3-cyano-7-ethoxy-6-quinolinyl)-3-[(2R)-1-methyl-2-pyrrolidinyl]acrylamide);

Quizartinib (1-[5-(2-Methyl-2-propanyl)-1,2-oxazol-3-yl]-3-(4-{7-[2-(4-morpholinyl)ethoxy]imidazo[2,1-b][1,3]benzothiazol-2-yl}phenyl)urea);

Radotinib (4-Methyl-N-[3-(4-methylimidazol-1-yl)-5-(trifluoromethyl)phenyl]-3-[(4-pyrazin-2-ylpyrimidin-2-yl) amino]benzamide);

Ramucirumab (antibody, CAS Number 947687-13-0, UNII D99YVK4LOX);

Regorafenib (4-[4-({[4-Chloro-3-(trifluoromethyl)phenyl]carbamoyl}amino)-3-fluorophenoxy]-N-methylpyridine-2-carboxamide hydrate);

Ribociclib (7-Cyclopentyl-N,N-dimethyl-2-{[5-(1-piperazinyl)-2-pyridinyl]amino}-7H-pyrrolo[2,3-d]pyrimidine-6-carboxamide);

Ripasudil (4-Fluoro-5-{[(2S)-2-methyl-1,4-diazepan-1-yl]sulfonyl}isoquinoline);

Ripretinib (3-{4-bromo-5-[1-ethyl-7-(methylamino)-2-oxo-1,2-dihydro-1,6-naphthyridin-3-yl]-2-fluorophenyl}-1-phenylurea);

Ritlecitinib (1-[(2S,5R)-2-methyl-5-(7H-pyrrolo[2,3-d]pyrimidin-4-ylamino)piperidin-1-yl]prop-2-en-1-one);

Ruxolitinib ((3R)-3-Cyclopentyl-3-[4-(7H-pyrrolo[2,3-d]pyrimidin-4-yl)pyrazol-1-yl]propanenitrile);

Savolitinib (3-[(1S)-1-Imidazo[1,2-a]pyridin-6-ylethyl]-5-(1-methylpyrazol-4-yl)triazolo[4,5-b]pyrazine);

Selpercatinib (6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile);

Selumetinib (6-(4-bromo-2-chloroanilino)-7-fluoro-N-(2-hydroxyethoxy)-3-methylbenzimidazole-5-carboxamide);

Simotinib (N-(3-chloro-4-fluorophenyl)-6-[2-(5,8-dioxa-10-azadispiro[2.0.44.33]undecan-10-yl)ethoxy]-7-methoxyquinazolin-4-amine);

Sirolimus ((1R,9S,12S,15R,16E,18R,19R,21R,23S,24E,26E,28E,30S,32S,35R)-1,18-dihydroxy-12-[(2R)-1-[(1S,3R,4R)-4-hydroxy-3-methoxycyclohexyl]propan-2-yl]-19,30-dimethoxy-15,17,21,23,29,35-hexamethyl-11,36-dioxa-4-azatricyclo[30.3.1.04,9]hexatriaconta-16,24,26,28-tetraene-2,3,10,14,20-pentone);

Sorafenib (4-[4-[[4-chloro-3-(trifluoromethyl)phenyl]carbamoylamino]phenoxy]-N-methyl-pyridine-2-carboxamide);

Sotorasib (6-Fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl)piperazin-1-yl]pyrido[2,3-d]pyrimidin-2(1H)-one);

Sunitinib (N-(2-Diethylaminoethyl)-5-[(Z)-(5-fluoro-2-oxo-1H-indol-3-ylidene)methyl]-2,4-dimethyl-1H-pyrrole-3-carboxamide);

Surufatinib (N-[2-(Dimethylamino)ethyl]-1-[3-[[4-[(2-methyl-1H-indol-5-yl)oxy]pyrimidin-2-yl]amino]phenyl]methanesulfonamide);

Temsirolimus ((1R,2R,4S)-4-{(2R)-2-[(3S,6R,7E,9R,10R,12R,14S,15E,17E,19E,21S,23S,26R,27R,34aS)-9,27-dihydroxy-10,21-dimethoxy-6,8,12,14,20,26-hexamethyl-1,5,11,28,29-pentaoxo-1,4,5,6,9,10,11,12,13,14,21,22,23,24,25,26,27,28,29,31,32,33,34,34a-tetracosahydro-3H-23,27-epoxypyrido[2,1-c][1,4]

oxazacyclohentriacontin-3-yl]propyl}-2-methoxycyclohexyl 3-hydroxy-2-(hydroxymethyl)-2-methylpropanoate);

Tenalisib (3-(3-Fluorophenyl)-2-[(1S)-1-(9H-purin-6-ylamino)propyl]-4H-chromen-4-one);

Tepotinib (3-{1-[(3-{5-[(1-methylpiperidin-4-yl)methoxy]pyrimidin2-yl}phenyl)methyl]-6-oxo-1,6-dihydropyridazin3-yl}benzonitrile);

Tirabrutinib (6-Amino-9-[(3R)-1-but-2-ynoylpyrrolidin-3-yl]-7-(4-phenoxyphenyl)purin-8-one);

Tirbanibulin (N-benzyl-2-[5-[4-(2-morpholin-4-ylethoxy)phenyl]pyridin-2-yl]acetamide);

Tivozanib (1-[2-chloro-4-(6,7-dimethoxyquinolin-4-yl)oxyphenyl]-3-(5-methyl-1,2-oxazol-3-yl)urea;

Tofacitinib (3-[(3R,4R)-4-Methyl-3-[methyl(7H-pyrrolo[2,3-d]pyrimidin-4-yl)amino]piperidin-1-yl]-3-oxopropanenitrile);

Trametinib (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H)-yl}phenyl)acetamide);

Trastuzumab (antibody, CAS Number 180288-69-1, UNII P188ANX8CK);

Trilaciclib (4-[[5-(4-methylpiperazin-1-yl)pyridin-2-yl]amino]spiro[1,3,5,11-tetrazatricyclo[7.4.0.02,7]trideca-2,4,6,8-tetraene-13,1'-cyclohexane]-10-one);

Tucatinib (6-N-(4,4-dimethyl-5H-1,3-oxazol-2-yl)-4-N-[3-methyl-4-([1,2,4]triazolo[1,5-a]pyridin-7-yloxy)phenyl]quinazoline-4,6-diamine);

Umbralisib (2-[(1S)-1-[4-Amino-3-(3-fluoro-4-propan-2-yloxyphenyl)pyrazolo[3,4-d]pyrimidin-1-yl]ethyl]-6-fluoro-3-(3-fluorophenyl)chromen-4-one);

Upadacitinib ((3S,4R)-3-Ethyl-4-(3H-imidazo[1,2-a]pyrrolo[2,3-e]pyrazin-8-yl)-N-(2,2,2-trifluoroethyl)pyrrolidine-1-carboxamide);

Vandetanib (N-(4-bromo-2-fluorophenyl)-6-methoxy-7-[(1-methylpiperidin-4-yl)methoxy]quinazolin-4-amine);

Vemurafenib (N-(3-{[5-(4-Chlorophenyl)-1H-pyrrolo[2,3-b]pyridin-3-yl]carbonyl1}-2,4-difluorophenyl)propane-1-sulfonamide);

Volasertib (N-((1S,4S)-4-(4-(cyclopropylmethyl)piperazin-1-yl)cyclohexyl)-4-(((R)-7-ethyl-8-isopropyl-5-methyl-6-oxo-5,6,7,8-tetrahydropteridin-2-yl)amino)-3-methoxybenzamide);

Zanubrutinib ((7S)-2-(4-phenoxyphenyl)-7-(1-prop-2-enoylpiperidin-4-yl)-4,5,6,7-tetrahydropyrazolo[1,5-a]pyrimidine-3-carboxamide); and mixtures thereof.

In some embodiments, the present disclosure provides a method of synthesizing a composition for delivery of an active agent to a cell in a target tissue of a subject in need thereof, which comprises: providing a porous particle, wherein the porous particle comprises a plurality of microscale reservoirs and a host molecular structure is adhered to a surface of the porous particle; providing an active agent; and mixing the active agent with the porous particle in a liquid medium. In some embodiments, the host molecular structure has a structure of Formula 1, wherein:

Formula 1

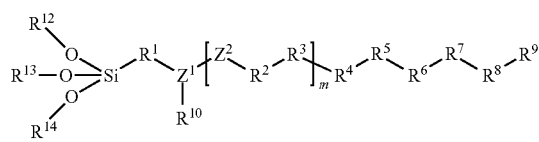

$R^1$ is —($C_1$-$C_6$)alkylene-, or —H;

$Z^1$ is —(N—)—, —H, or none;

$Z^2$ is —CO—, —SO$_2$—, or none;

$R^2$ is —(C(—H)—$R^{11}$)—, —($C_1$-$C_3$)alkylene, —(C(—H)—((($C_1$-$C_6$)alkylene-(C(=O)(—O⁻X))))—, —(C(—H)(—($C_1$-$C_6$)alkylene-Ar$^1$))—, —O—, —H, or none;

$R^3$ is —(CH$_2$)—, —(N(—H))—, —H, or none;

$R^4$ is —(CH$_2$)—, —(C(=O))—, —H, or none;

$R^5$ is —($C_1$-$C_{20}$)alkylene-, —($C_1$-$C_3$)alkylene-Ar$^2$, —O—, —H, or none;

$R^6$ is —(CH$_2$)—, —H, or none;

$R^7$ is —(CH$_2$)—, —(C(=O))—, —H, or none;

$R^8$ is —(CH$_2$)—, —(N(—H))—, —H, or none;

$R^9$ is —($C_1$-$C_3$)alkylene-Ar$^2$, —(C(=O)(—O⁻X)), ($C_1$-$C_{20}$)alkylene-(C(=O)(—O⁻X)), ($C_1$-$C_{20}$)alkyl, —H, or none;

$R^{10}$ is —($C_1$-$C_6$)alkylene, or —H;

$R^{11}$ is side chain of amino acid such as methyl group (—CH$_3$), guanidino group (—(CH$_2$)$_3$—NH—C(=NH)—NH$_2$), amide group (—CH$_2$—CONH$_2$), (—CH$_2$—CH$_2$—CONH$_2$), carboxyl group (—CH$_2$—COOH), (—CH$_2$—CH$_2$—COOH), thiol group (—CH$_2$—SH), amide group (—CH$_2$—CH$_2$—CONH$_2$), carboxyl group (—CH$_2$—CH$_2$—COOH), hydrogen atom (—H), imidazole group (—CH$_2$—C$_3$H$_3$N$_2$), sec-butyl group (—CH(CH$_3$)—CH$_2$—CH$_3$), isobutyl group (—CH$_2$—CH(CH$_3$)$_2$), amino group (—(CH$_2$)$_4$—NH$_2$), (—(CH$_2$)$_3$—NH$_2$), thioether group (—CH$_2$—CH$_2$—S—CH$_3$), hydroxymethyl group (—CH$_2$—OH), hydroxyethyl group (—CH(OH)—CH$_3$), hydroxyphenyl group (—CH$_2$—C$_6$H$_4$—OH), isopropyl group (—CH(CH$_3$)$_2$), or their derivative;

m is 0~150;

provided that if m>2, then Ar$^1$ or R$^{11}$ can be chosen independently;

Ar$^1$ is a substituted phenyl, an unsubstituted phenyl, a substituted indole, or an unsubstituted indole;

Ar$^2$ is a substituted phenyl, an unsubstituted phenyl, a substituted naphthyl, an unsubstituted naphthyl, a substituted indole, or an unsubstituted indole; and X is H$^+$, Na$^+$, Ca$^+$, or K$^+$, and wherein R$^{12}$, R$^{13}$, and R$^{14}$, each independently, represents the surface of the porous particle or an adjacent silane.

In some embodiments, the method of synthesizing a composition according to the present disclosure further comprises: providing the host molecular structure of Formula 1 by reacting a molecular structure of Formula 6 with a molecule of Formula 7, wherein Formula 6

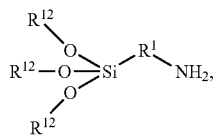

Formula 7

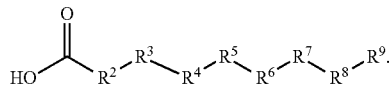

In some embodiments, providing the host molecular structure of Formula 1 by reacting a molecular structure of Formula 6 with a molecule of Formula 7 is performed in the presence of a carbodiimide or another peptide coupling reagent.

In some embodiments, the method of synthesizing a composition according to the present disclosure further comprises: providing the host molecular structure having a structure of Formula 1 by reacting a molecule of Formula 8 with the surface of the porous particle, Formula 8

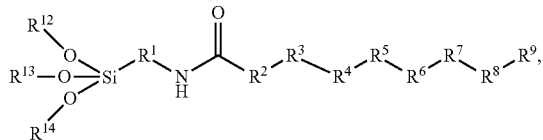

wherein $R^{12}$ is a $(C_1-C_3)$alkyl.

In some embodiments of the synthesis method, a weight percentage of about 1.0 wt % to about 10.0 wt %, including about 1.5 wt % to about 10.0 wt %, about 2.0 wt % to about 10.0 wt %, about 2.5 wt % to about 10.0 wt %, about 3.0 wt % to about 10.0 wt %, about 3.5 wt % to about 10.0 wt %, about 4.0 wt % to about 10.0 wt %, about 4.5 wt % to about 10.0 wt %, about 5.0 wt % to about 10.0 wt %, about 5.5 wt % to about 10.0 wt %, about 6.0 wt % to about 10.0 wt %, about 6.5 wt % to about 10.0 wt %, about 7.0 wt % to about 10.0 wt %, about 7.5 wt % to about 10.0 wt %, about 8.0 wt % to about 10.0 wt %, about 8.5 wt % to about 10.0 wt %, about 9.0 wt % to about 10.0 wt %, about 1.0 wt % to about 8.0 wt %, about 1.0 wt % to about 7.0 wt %, about 1.0 wt % to about 6.0 wt %, about 1.0 wt % to about 5.0 wt %, about 1.0 wt % to about 4.0 wt %, about 2.0 wt % to about 6.0 wt % and about 3.0 wt % to about 5.0 wt % of the active agent is mixed with the porous particle in a liquid medium, based on a total weight of the composition in the liquid medium.

In some embodiments of the synthesis method, the liquid medium includes water, methanol, ethanol, propanol, dimethylsulfoxide (DMSO), or a mixture thereof.

In some embodiments of the synthesis method, the active agent includes a kinase inhibitor selected from the group consisting of Abemaciclib, Abrocitinib, Acalabrutinib, Afatinib, Alectinib, Almonertinib, Alpelisib, Amivantamab, Apatinib, Asciminib, Avapritinib, Axitinib, Baricitinib, Binimetinib, Bosutinib, Brigatinib, Cabozantinib, Capivasertib, Capmatinib, Catequentinib, Ceritinib, Cetuximab, Cobimetinib, Copanlisib, Crizotinib, Dabrafenib, Dacomitinib, Dasatinib, Defactinib, Delgocitinib, Deucravacitinib, Duvelisib, Encorafenib, Entrectinib, Erdafitinib, Erlotinib, Everolimus, Fasudil, Fedratinib, Filgotinib, Flumatinib, Fostamatinib, Fostamatinib, Fruquintinib, Furmonertinib, Futibatinib, Gefitinib, Gilteritinib, Ibrutinib, Icotinib, Idelalisib, Imatinib, Infigratinib, Ivosidenib, Lapatinib, Larotrectinib, Lazertinib, Leniolisib, Lenvatinib, Lorlatinib, Margetuximab, Midostaurin, Mobocertinib, Necitumumab, Neratinib, Netarsudil, Nilotinib, Nimotuzumab, Nintedanib, Olaratumab, Olmutinib, Orelabrutinib, Osimertinib, Pacritinib, Palbociclib, Panitumumab, Paxalisib, Pazopanib, Peficitinib, Pemigatinib, Pertuzumab, Pexidartinib, Pirtobrutinib, Ponatinib, Pralsetinib, Pyrotinib, Quizartinib, Radotinib, Ramucirumab, Regorafenib, Ribociclib, Ripasudil, Ripretinib, Ritlecitinib, Ruxolitinib, Savolitinib, Selpercatinib, Selumetinib, Simotinib, Sirolimus, Sorafenib, Sotorasib, Sunitinib, Surufatinib, Temsirolimus, Tenalisib, Tepotinib, Tirabrutinib, Tirbanibulin, Tivozanib, Tofacitinib, Trametinib, Trastuzumab, Trilaciclib, Tucatinib, Umbralisib, Upadacitinib, Vandetanib, Vemurafenib, Volasertib, Zanubrutinib, and mixtures thereof.

In some embodiments, the present disclosure provides a method of treating a medical disorder in a subject in need thereof, which comprises: administering to the subject in need thereof a composition, wherein the composition includes an active agent; and a porous particle, wherein the porous particle comprises a plurality of microscale reservoirs and a host molecular structure is adhered to a surface of the porous particle. In some embodiments, the host molecular structure has a structure of Formula 1, wherein:

Formula 1

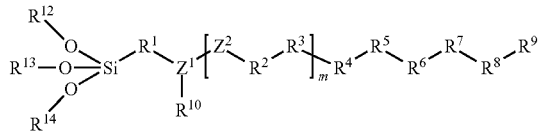

$R^1$ is —$(C_1-C_6)$alkylene-, or —H;
$Z^1$ is —(N—)—, —H, or none;
$Z^2$ is —CO—, —$SO_2$—, or none;
$R^2$ is —(C(—H)—$R^{11}$)—, —$(C_1-C_3)$alkylene, —(C(—H)—$((C_1-C_6)$alkylene-(C(=O)(—O⁻X))))—, —(C(—H)(—$(C_1-C_6)$alkylene-Ar¹))—, —O—, —H, or none;
$R^3$ is —$(CH_2)$—, —(N(—H))—, —H, or none;
$R^4$ is —$(CH_2)$—, —(C(=O))—, —H, or none;
$R^5$ is —$(C_1-C_{20})$alkylene-, —$(C_1-C_3)$alkylene-Ar², —O—, —H, or none;
$R^6$ is —$(CH_2)$—, —H, or none;
$R^7$ is —$(CH_2)$—, —(C(=O))—, —H, or none;
$R^8$ is —$(CH_2)$—, —(N(—H))—, —H, or none;
$R^9$ is —$(C_1-C_3)$alkylene-Ar², —(C(=O)(—O⁻X)), $(C_1-C_{20})$alkylene-(C(=O)(—O⁻X)), —$(C_1-C_{20})$alkyl, —H, or none;
$R^{10}$ is —$(C_1-C_6)$alkylene, or —H;
$R^{11}$ is side chain of amino acid such as methyl group (—$CH_3$), guanidino group (—$(CH_2)_3$—NH—C(=NH)—$NH_2$), amide group (—$CH_2$—$CONH_2$), (—$CH_2$—$CH_2$—$CONH_2$), carboxyl group (—$CH_2$—COOH), (—$CH_2$—$CH_2$—COOH), thiol group (—$CH_2$—SH), amide group (—$CH_2$—$CH_2$—$CONH_2$), carboxyl group (—$CH_2$—$CH_2$—COOH), hydrogen atom (—H), imidazole group (—$CH_2$—$C_3H_3N_2$), sec-butyl group (—CH($CH_3$)—$CH_2$—$CH_3$), isobutyl group (—$CH_2$—CH($CH_3$)$_2$), amino group (—$(CH_2)_4$—$NH_2$), (—$(CH_2)_3$—$NH_2$), thioether group (—$CH_2$—$CH_2$—S—$CH_3$), hydroxymethyl group (—$CH_2$—OH), hydroxyethyl group (—CH(OH)—$CH_3$), hydroxyphenyl group (—$CH_2$-$C_6H_4$—OH), isopropyl group (—CH($CH_3$)$_2$), or their derivative;
m is 0~150;
provided that if m>2, then Ar¹ or $R^{11}$ can be chosen independently;
Ar¹ is a substituted phenyl, an unsubstituted phenyl, a substituted indole, or an unsubstituted indole;
Ar² is a substituted phenyl, an unsubstituted phenyl, a substituted naphthyl, an unsubstituted naphthyl, a substituted indole, or an unsubstituted indole; and
X is H⁺, Na⁺, Ca⁺, or K⁺, and
wherein $R^{12}$, $R^{13}$, and $R^{14}$, each independently, represents the surface of the porous particle or an adjacent silane.

In some embodiments of the treatment method, the active agent includes a kinase inhibitor selected from the group consisting of Abemaciclib, Abrocitinib, Acalabrutinib, Afatinib, Alectinib, Almonertinib, Alpelisib, Amivantamab, Apatinib, Asciminib, Avapritinib, Axitinib, Baricitinib, Binimetinib, Bosutinib, Brigatinib, Cabozantinib, Capivasertib, Capmatinib, Catequentinib, Ceritinib, Cetuximab, Cobimetinib, Copanlisib, Crizotinib, Dabrafenib, Dacomitinib, Dasatinib, Defactinib, Delgocitinib, Deucravacitinib, Duvelisib, Encorafenib, Entrectinib, Erdafitinib, Erlotinib, Everolimus, Fasudil, Fedratinib, Filgotinib, Flumatinib, Fostamatinib, Fostamatinib, Fruquintinib, Furmonertinib, Futibatinib, Gefitinib, Gilteritinib, Ibrutinib, Icotinib, Idelalisib, Imatinib, Infigratinib, Ivosidenib, Lapatinib, Larotrectinib, Lazertinib, Leniolisib, Lenvatinib, Lorlatinib, Margetuximab, Midostaurin, Mobocertinib, Necitumumab, Neratinib, Netarsudil, Nilotinib, Nimotuzumab, Nintedanib, Olaratumab, Olmutinib, Orelabrutinib, Osimertinib, Pacritinib, Palbociclib, Panitumumab, Paxalisib, Pazopanib, Peficitinib, Pemigatinib, Pertuzumab, Pexidartinib, Pirtobrutinib, Ponatinib, Pralsetinib, Pyrotinib, Quizartinib, Radotinib, Ramucirumab, Regorafenib, Ribociclib, Ripasudil, Ripretinib, Ritlecitinib, Ruxolitinib, Savolitinib, Selpercatinib, Selumetinib, Simotinib, Sirolimus, Sorafenib, Sotorasib, Sunitinib, Surufatinib, Temsirolimus, Tenalisib, Tepotinib, Tirabrutinib, Tirbanibulin, Tivozanib, Tofacitinib, Trametinib, Trastuzumab, Trilaciclib, Tucatinib, Umbralisib, Upadacitinib, Vandetanib, Vemurafenib, Volasertib, Zanubrutinib, and mixtures thereof.

In some embodiments of the treatment method, the medical disorder is selected from the group consisting of Atopic dermatitis, Mantle cell lymphoma, non-small cell lung cancer (NSCLC) with epidermal growth factor receptor (EGFR) mutations, NSCLC with anaplastic lymphoma kinase (ALK) translocations, Advanced mutation+ve NSCLC, Breast cancer, hormone receptor (HR)+ve, human epidermal growth factor receptor 2 (HER2)-ve, NSCLC, Gastric cancer, NSCLC, Chronic myelogenous leukemia, platelet-derived growth factor receptor (PDGFR) exon 18 mutation (incl D842V)+ve, Renal Cell Carcinoma, Rheumatoid arthritis, B-subgroup rapidly accelerated fibrosarcoma (BRAF) mutant melanoma, Chronic Myelogenous Leukemia, ALK-rearranged metastatic NSCLC, Medullary Thyroid Cancer, HR+ and phosphoinositide 3-kinase (PI3K) mutation breast cancer, mesenchymal-epithelial transition (MET) mutation+ve NSCLC, EGFR colorectal cancer, Melanoma, breast cancer, Follicular lymphoma, NSCLC with Alkmutation, Skin cancer, NSCLC with EGFR mutations, Chronic Myelogenous Leukemia, Solid tumors, Psoriasis, chronic lymphocytic leukemia (CLL), small lymphocytic lymphoma (SLL), follicular lymphoma (FL), BRAF mutant melanoma, ROS proto-oncogene 1 (ROS1)+ve NSCLC, solid tumors neurotrophic tyrosine receptor kinase (NTRK)+ve, Advanced metastatic urothelial carcinoma, Pancreatic Cancer, Renel Cell Carcinoma, Cerebral Vasospasm pulmonary arterial hypertension (PAH), myelofibrosis, Rheumatoid arthritis, Chronic myelogenous leukemia, Autoimmune thrombocytopenia, Chronic immune thrombocytopenia, Metastatic colorectal cancer, Cholangiocarcinoma, Acute myeloid leukemia FLT3 (fms-like tyrosine kinase 3) mutant, Mantle cell lymphoma, chronic lymphocytic leukemia, Chronic Myelogenous Leukemia, Acute myeloid leukemia (AML), Breast Cancer, Solid tumours with NTRK fusions, Activated phosphoinositide 3-kinase delta syndrome (APDS), PASLI (p110 delta activating mutation causing senescent T cells), lymphadenopathy, immunodeficiency, Differentiated Thyroid cancer (DTC) kidney cancer, ALK+ ve met NSCLC, murine HER2 (MHER2)-positive breast cancer, Acute myeloid leukemia (FLT3 mutation-positive), NSCLC with EGFR mutations, HER2-positive breast cancer, Glaucoma (topical), Chronic Myelogenous Leukemia, cell carcinomas of the head and neck, Idiopathic pulmonary fibrosis, Soft tissue sarcoma, T790M+ve NSCLC, mantle cell lymphoma CLL, SLL, T790M+ve NSCLC, Myelofibrosis, Advanced (metastatic) breast cancer, EGFR colorectal cancer, Malignant glioblastoma, Renal cancer, Rhematoid arthritis, Cholangiocarcinoma with FGFR2 (fibroblast growth factor receptor 2) fusionA, HER2-positive breast cancer, Tenosynovial giant cell tumor, Mantle Cell Lymphoma, Chronic Myelogenous Leukemia, Acute lymphoblastic leukemia (ALL), Met RET fusion+ve NSCLC medullary thyroid cancer (MTC), Breast cancer, Acute myeloid leukemia, Chronic Myelogenous Leukemia, metastatic non-small cell lung cancer (MNSCLC) colorectal cancer, Colorectal Cancer GIST (gastrointestinal stromal tumor), HCC, Advanced (metastatic) breast cancer HR+ve, HER2-ve, Glaucoma ocular hypertension, Advanced GIST Mastocytosis, Severe alopecia, Myelofibrosis, Adenocarcinoma, NSCLC, NSCLC, MTC, thyroid cancers, Neurofibromatosis type 1, Solid tumors, kidney Transplantation, Renal Cancer HCC (hepatocellular carcinoma), KRAS non-small-cell lung cancer, Renal Cancer, Imatinib resistant GIST, Advanced pancreatic NET (neuroendocrine tumor), Advanced Renal Cell Carcinoma, Peripheral T-cell lymphoma (PTCL), breast cancer, Metastatic NSCLC, Chronic myelogenous leukemia, Actinic keratosis, Advanced RCC (Renal cell carcinoma), Rheumatoid arthritis, M-Melanoma with BRAFV600E, EGFR breast cancer, SCLC (small cell lung cancer) chemo Myelopreservation, HER2-positive breast cancer, Marginal zone lymphoma, Rheumatoid arthritis, Thyroid Cancer, Metastatic Melanoma BRAFV600E, Acute myeloid leukemia, and mantle cell lymphoma.

In some embodiments, the method of treating further comprises releasing the active agent within a cell in a target tissue by passing the composition into an interior of the target tissue. In some embodiments, a cell in a target tissue is a cancer cell or a cell located within a tumor.

FURTHER DISCUSSION OF EMBODIMENTS

Embodiment 1. A composition for delivery of an active agent to a cell in a target tissue of a subject in need thereof, comprising:
　an active agent; and
　a porous particle, wherein the porous particle comprises a plurality of microscale reservoirs and a host molecular structure is adhered to a surface of the porous particle, wherein the host molecular structure has a structure of Formula 1,
　wherein:

Formula 1

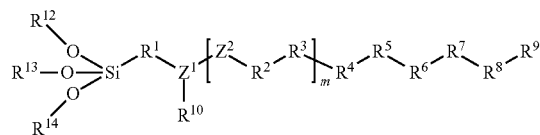

$R^1$ is —$(C_1-C_6)$alkylene-, or —H;
$Z^1$ is —(N—)—, —H, or none;
$Z^2$ is —(C(=O))—, —SO$_2$—, or none;
$R^2$ is —(C(—H)—$R^{11}$)—, —$(C_1-C_3)$alkylene, —(C(—H)—(($C_1-C_6$)alkylene-(C(=O)(—O⁻X))))—, —(C(—H)(—$(C_1-C_6)$alkylene-Ar$^1$)), —O—, —H, or none;

R³ is —(CH₂)—, —(N(—H))—, —H, or none;
R⁴ is —(CH₂)—, —(C(=O))—, —H, or none;
R⁵ is —(C₁-C₂₀)alkylene-, —(C₁-C₃)alkylene-Ar², —O—, —H, or none;
R⁶ is —(CH₂)—, —H, or none;
R⁷ is —(CH₂)—, —(C(=O))—, —H, or none;
R⁸ is —(CH₂)—, —(N(—H))—, —H, or none;
R⁹ is —(C₁-C₃)alkylene-Ar², —(C(=O)(—O⁻X)), (C₁-C₂₀)alkylene-(C(=O)(—O⁻X)), —(C₁-C₂₀)alkyl, —H, or none;
R¹⁰ is —(C₁-C₆)alkyl, or —H;
R¹¹ is side chain of amino acid such as methyl group (—CH₃), guanidino group (—(CH₂)₃—NH—C(=NH)—NH₂), amide group (—CH₂—CONH₂), (—CH₂—CH₂—CONH₂), carboxyl group (—CH₂—COOH), (—CH₂—CH₂—COOH), thiol group (—CH₂—SH), amide group (—CH₂—CH₂—CONH₂), carboxyl group (—CH₂—CH₂—COOH), hydrogen atom (—H), imidazole group (—CH₂—C₃H₃N₂), sec-butyl group (—CH(CH₃)—CH₂—CH₃), isobutyl group (—CH₂—CH(CH₃)₂), amino group (—(CH₂)₄—NH₂), (—(CH₂)₃—NH₂), thioether group (—CH₂—CH₂—S—CH₃), hydroxymethyl group (—CH₂—OH), hydroxyethyl group (—CH(OH)—CH₃), hydroxyphenyl group (—CH₂-C₆H₄—OH), isopropyl group (—CH(CH₃)₂), or their derivative;
m is 0~150;
provided that if m>2, then Ar¹ or R¹¹ can be chosen independently;
Ar¹ is a substituted phenyl, an unsubstituted phenyl, a substituted indole, or an unsubstituted indole;
Ar² is a substituted phenyl, an unsubstituted phenyl, a substituted naphthyl, an unsubstituted naphthyl, a substituted indole, or an unsubstituted indole; and
X is H⁺, Na⁺, Ca⁺, or K⁺, and R¹², R¹³, and R¹⁴, each independently, represents the surface of the porous particle or an adjacent silane.

Embodiment 2. The composition of one or more of Embodiments 1-9, wherein:
Z¹ is —(N—)—;
Z² is —(C(=O))—;
R² is —(C(—H)(—(C₁-C₆)alkylene-Ar¹)) and Ar¹ is an unsubstituted phenyl;
R³ is —(N(—H))—;
R⁴ is —(C(=O))—;
R⁹ is —(C₁-C₂₀)alkylene-(C(=O)(—O⁻X)); and
R¹⁰ is —H.

Embodiment 3. The composition of one or more of Embodiments 1-9, wherein:
Z¹ is —(N—)—;
Z² is —(C(=O))—;
R² is —(C(—H)—((C₁-C₆)alkylene-(C(=O)(—O⁻X))));
R³ is —(N(—H))—;
R⁴ is —(C(=O))—;
R⁷ is —(C(=O))—;
R⁹ is —(C₁-C₃)alkylene-Ar² and Ar² is an unsubstituted phenyl; and
R¹⁰ is —H.

Embodiment 4. The composition of one or more of Embodiments 1-9, wherein:
Z¹ is —(N—)—;
Z² is —(C(=O))—;
R⁹ is —(C₁-C₃)alkylene-Ar², —(C(=O)(—O⁻X)), (C₁-C₂₀)alkylene-(C(=O)(—O⁻X)), or (C₁-C₂₀)alkyl; and
R¹⁰ is H;

Embodiment 5. The composition of one or more of Embodiments 1-9, wherein the host molecular structure has a structure of Formula 2, Formula 3, Formula 4, or Formula 5, or mixture thereof:

Formula 2
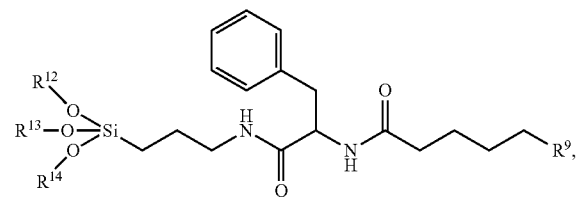

wherein R⁹ is —(C₁-C₂₀)alkylene-(C(=O)(—O⁻X));

Formula 3
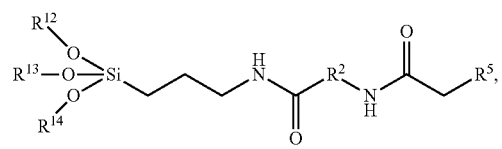

R² is —(C(—H)—((C₁-C₆)alkylene-(C(=O)(—O⁻X)))) and R⁵ is —(C₁-C₃)alkylene-Ar²;

Formula 4
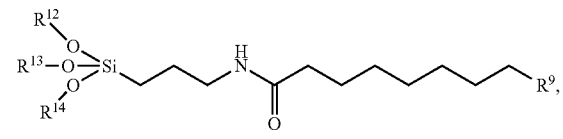

wherein R² is —(C₁-C₂₀)alkyl; and

Formula 5
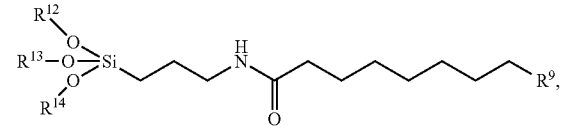

wherein R⁹ is —(C₁-C₂₀)alkylene-(C(=O)(—O⁻X));
wherein R¹², R¹³, and R¹⁴, each independently, represents the surface of the porous particle or an adjacent silane.

Embodiment 6. The composition of one or more of Embodiments 1-9, wherein the porous particle is a micro or a nano particle; or
wherein the porous particle is biocompatible and degradable; or
wherein the plurality of microscale reservoirs of the porous particle has a size ranging from about 0.3 μm to about 4 m; or
wherein the porous particle has a shape selected from the group consisting of discoidal, spheroid, non-spheroid, oblate spheroid, and combinations thereof; or
wherein the porous particle includes a porous oxide material or a porous etched material; or wherein the porous particle is able to overcome at least one biological barrier; or any combination thereof.

Embodiment 7. The composition of one or more of Embodiments 1-9, wherein the porous particle includes a porous oxide material selected from the group consisting of porous silica, porous aluminum oxide, porous titanium oxide, porous iron oxide, and combinations thereof; or
wherein the porous particle includes a porous etched material selected from the group consisting of porous silicon, porous silica, porous germanium, porous GaAs, porous InP, porous SiC, porous $Si_xGe_{1-x}$, porous GaP, porous GaN, and combinations thereof.

Embodiment 8. The composition of one or more of Embodiments 1-9, wherein the active agent includes a kinase inhibitor; or
wherein the surface of the porous particle includes an interior surface of a pore of the porous particle; or
wherein the active agent is retained for a longer duration at a retention pH by a porous particle having the molecular host structure than a porous particle or a porous particle that excludes the molecular host structure; or
wherein the active agent forms a non-covalent complex with the molecular host structure.

Embodiment 9. The composition of one or more of Embodiments 1-9, wherein the active agent includes a kinase inhibitor selected from the group consisting of Abemaciclib, Abrocitinib, Acalabrutinib, Afatinib, Alectinib, Almonertinib, Alpelisib, Amivantamab, Apatinib, Asciminib, Avapritinib, Axitinib, Baricitinib, Binimetinib, Bosutinib, Brigatinib, Cabozantinib, Capivasertib, Capmatinib, Catequentinib, Ceritinib, Cetuximab, Cobimetinib, Copanlisib, Crizotinib, Dabrafenib, Dacomitinib, Dasatinib, Defactinib, Delgocitinib, Deucravacitinib, Duvelisib, Encorafenib, Entrectinib, Erdafitinib, Erlotinib, Everolimus, Fasudil, Fedratinib, Filgotinib, Flumatinib, Fostamatinib, Fostamatinib, Fruquintinib, Furmonertinib, Futibatinib, Gefitinib, Gilteritinib, Ibrutinib, Icotinib, Idelalisib, Imatinib, Infigratinib, Ivosidenib, Lapatinib, Larotrectinib, Lazertinib, Leniolisib, Lenvatinib, Lorlatinib, Margetuximab, Midostaurin, Mobocertinib, Necitumumab, Neratinib, Netarsudil, Nilotinib, Nimotuzumab, Nintedanib, Olaratumab, Olmutinib, Orelabrutinib, Osimertinib, Pacritinib, Palbociclib, Panitumumab, Paxalisib, Pazopanib, Peficitinib, Pemigatinib, Pertuzumab, Pexidartinib, Pirtobrutinib, Ponatinib, Pralsetinib, Pyrotinib, Quizartinib, Radotinib, Ramucirumab, Regorafenib, Ribociclib, Ripasudil, Ripretinib, Ritlecitinib, Ruxolitinib, Savolitinib, Selpercatinib, Selumetinib, Simotinib, Sirolimus, Sorafenib, Sotorasib, Sunitinib, Surufatinib, Temsirolimus, Tenalisib, Tepotinib, Tirabrutinib, Tirbanibulin, Tivozanib, Tofacitinib, Trametinib, Trastuzumab, Trilaciclib, Tucatinib, Umbralisib, Upadacitinib, Vandetanib, Vemurafenib, Volasertib, Zanubrutinib, and mixtures thereof.

A composition of embodiments 1-9 for use as a medicine or medicament for treating a proliferative cellular disorder or a cancer, alleviating or reducing one or more of the symptoms of a proliferative cellular disorder or a cancer.

Using a composition of embodiments 1-9 as a medicine or medicament for treating a proliferative cellular disorder or a cancer, alleviating or reducing one or more of the symptoms of a proliferative cellular disorder or a cancer.

Embodiment 10. A method of synthesizing a composition for delivery of an active agent to a cell in a target tissue of a subject in need thereof, comprising: providing a porous particle, wherein the porous particle comprises a plurality of microscale reservoirs and a host molecular structure is adhered to a surface of the porous particle,
wherein the host molecular structure has a structure of Formula 1,

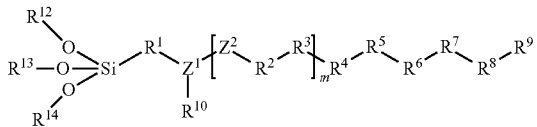

Formula 1 wherein:
$R^1$ is —$(C_1$-$C_6)$alkylene-, or —H;
$Z^1$ is —(N—)—, —H, or none;
$Z^2$ is —CO—, —$SO_2$—, or none;
$R^2$ is —(C(—H)—$R^{11}$)—, —$(C_1$-$C_3)$alkylene, —(C(—H)—(($C_1$-$C_6$)alkylene-(C(=O)(—$O^-$X))))—, —(C(—H)(—$(C_1$-$C_6)$alkylene-$Ar^1$)), —O—, —H, or none;
$R^3$ is —$(CH_2)$—, —(N(—H))—, —H, or none;
$R^4$ is —$(CH_2)$—, —(C(=O))—, —H, or none;
$R^5$ is —$(C_1$-$C_{20})$alkylene, —$(C_1$-$C_3)$alkylene-$Ar^2$, —O—, —H, or none;
$R^6$ is —$(CH_2)$—, —H, or none;
$R^7$ is —$(CH_2)$—, —(C(=O))—, —H, or none;
$R^8$ is —$(CH_2)$—, —(N(—H))—, —H, or none;
$R^9$ is —$(C_1$-$C_3)$alkylene-$Ar^2$, —(C(=O)(—$O^-$X)), ($C_1$-$C_{20}$)alkylene-(C(=O)(—$O^-$X)), —$(C_1$-$C_{20})$alkyl, —H, or none;
$R^{10}$ is —$(C_1$-$C_6)$alkylene, or —H;
$R^{11}$ is side chain of amino acid such as methyl group (—$CH_3$), guanidino group (—$(CH_2)_3$—NH—C(=NH)—$NH_2$), amide group (—$CH_2$—$CONH_2$), (—$CH_2$—$CH_2$—$CONH_2$), carboxyl group (—$CH_2$—COOH), (—$CH_2$—$CH_2$—COOH), thiol group (—$CH_2$—SH), amide group (—$CH_2$—$CH_2$—$CONH_2$), carboxyl group (—$CH_2$—$CH_2$—COOH), hydrogen atom (—H), imidazole group (—$CH_2$—$C_3H_3N_2$), sec-butyl group (—$CH(CH_3)$—$CH_2$—$CH_3$), isobutyl group (—$CH_2$—$CH(CH_3)_2$), amino group (—$(CH_2)_4$—$NH_2$), (—$(CH_2)_3$—$NH_2$), thioether group (—$CH_2$—$CH_2$—S—$CH_3$), hydroxymethyl group (—$CH_2$—OH), hydroxyethyl group (—CH(OH)—$CH_3$), hydroxyphenyl group (—$CH_2$-$C_6H_4$—OH), isopropyl group (—$CH(CH_3)_2$), or their derivative;
m is 0~150;
provided that if m>2, then $Ar^1$ or $R^{11}$ can be chosen independently;
$Ar^1$ is a substituted phenyl, an unsubstituted phenyl, a substituted indole, or an unsubstituted indole;
$Ar^2$ is a substituted phenyl, an unsubstituted phenyl, a substituted naphthyl, an unsubstituted naphthyl, a substituted indole, or an unsubstituted indole; and
X is $H^+$, $Na^+$, $Ca^+$, or $K^+$, and
wherein $R^{12}$, $R^{13}$, and $R^{14}$, each independently, represents the surface of the porous particle or an adjacent silane;
providing an active agent; and
mixing the active agent with the porous particle in a liquid medium.

Embodiment 11. The method of one or more of Embodiments 10-13, further comprising:
providing the host molecular structure of Formula 1 by reacting a molecular structure of Formula 6 with a molecule of Formula 7, wherein

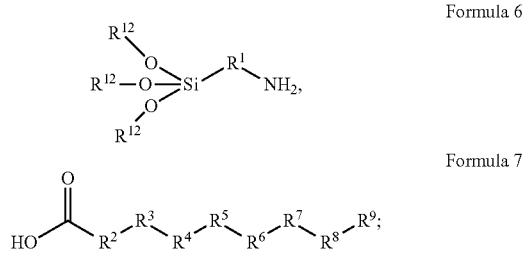

Formula 6

Formula 7 providing the host molecular structure having a structure of Formula 1 by reacting a molecule of Formula 8 with the surface of the porous particle,

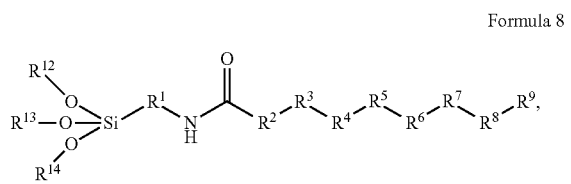

Formula 8 wherein $R^{12}$ is a $(C_1-C_3)$alkyl.

Embodiment 12. The method of one or more of Embodiments 10-13, wherein providing the host molecular structure of Formula 1 by reacting a molecular structure of Formula 6 with a molecule of Formula 7 is performed in the presence of a carbodiimide or another peptide coupling reagent.

Embodiment 13. The method of one or more of Embodiments 10-13, wherein the active agent includes a kinase inhibitor selected from the group consisting of Abemaciclib, Abrocitinib, Acalabrutinib, Afatinib, Alectinib, Almonertinib, Alpelisib, Amivantamab, Apatinib, Asciminib, Avapritinib, Axitinib, Baricitinib, Binimetinib, Bosutinib, Brigatinib, Cabozantinib, Capivasertib, Capmatinib, Catequentinib, Ceritinib, Cetuximab, Cobimetinib, Copanlisib, Crizotinib, Dabrafenib, Dacomitinib, Dasatinib, Defactinib, Delgocitinib, Deucravacitinib, Duvelisib, Encorafenib, Entrectinib, Erdafitinib, Erlotinib, Everolimus, Fasudil, Fedratinib, Filgotinib, Flumatinib, Fostamatinib, Fostamatinib, Fruquintinib, Furmonertinib, Futibatinib, Gefitinib, Gilteritinib, Ibrutinib, Icotinib, Idelalisib, Imatinib, Infigratinib, Ivosidenib, Lapatinib, Larotrectinib, Lazertinib, Leniolisib, Lenvatinib, Lorlatinib, Margetuximab, Midostaurin, Mobocertinib, Necitumumab, Neratinib, Netarsudil, Nilotinib, Nimotuzumab, Nintedanib, Olaratumab, Olmutinib, Orelabrutinib, Osimertinib, Pacritinib, Palbociclib, Panitumumab, Paxalisib, Pazopanib, Peficitinib, Pemigatinib, Pertuzumab, Pexidartinib, Pirtobrutinib, Ponatinib, Pralsetinib, Pyrotinib, Quizartinib, Radotinib, Ramucirumab, Regorafenib, Ribociclib, Ripasudil, Ripretinib, Ritlecitinib, Ruxolitinib, Savolitinib, Selpercatinib, Selumetinib, Simotinib, Sirolimus, Sorafenib, Sotorasib, Sunitinib, Surufatinib, Temsirolimus, Tenalisib, Tepotinib, Tirabrutinib, Tirbanibulin, Tivozanib, Tofacitinib, Trametinib, Trastuzumab, Trilaciclib, Tucatinib, Umbralisib, Upadacitinib, Vandetanib, Vemurafenib, Volasertib, Zanubrutinib, and mixtures thereof; or wherein a weight percentage of about 1.0 wt % to about 10.0 wt % of the active agent is mixed with the porous particle in a liquid medium, based on a total weight of the composition in the liquid medium; or wherein the liquid medium includes water, methanol, ethanol, propanol, dimethylsulfoxide (DMSO), or a mixture thereof.

Embodiment 14. A method of treating a medical disorder in a subject in need thereof, comprising:
administering to the subject in need thereof a composition,
wherein the composition includes an active agent; and
a porous particle, wherein the porous particle comprises a plurality of microscale reservoirs and a host molecular structure is adhered to a surface of the porous particle,
wherein the host molecular structure has a structure of Formula 1,
wherein:

Formula 1

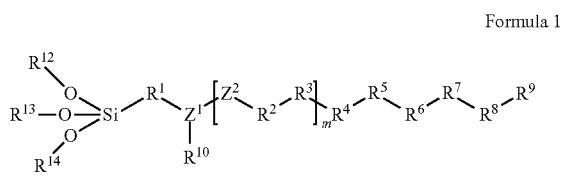

$R^1$ is —$(C_1-C_6)$alkylene-, or —H;
$Z^1$ is —(N—)—, —H, or none;
$Z^2$ is —CO—, —SO$_2$—, or none;
$R^2$ is —(C(—H)—$R^{11}$)—, —$(C_1-C_3)$alkylene, —(C(—H)—$((C_1-C_6)$alkylene-(C(=O)(—O$^-$X))))—, —(C(—H)(—$(C_1-C_6)$alkylene-Ar$^1$)), —O—, —H, or none;
$R^3$ is —(CH$_2$)—, —(N(—H))—, —H, or none;
$R^4$ is —(CH$_2$)—, —(C(=O))—, —H, or none;
$R^5$ is —$(C_1-C_{20})$alkylene-, —$(C_1-C_3)$alkylene-Ar$^2$, —O—, —H, or none;
$R^6$ is —(CH$_2$)—, —H, or none;
$R^7$ is —(CH$_2$)—, —(C(=O))—, —H, or none;
$R^8$ is —(CH$_2$)—, —(N(—H))—, —H, or none;
$R^9$ is —$(C_1-C_3)$alkylene-Ar$^2$, —(C(=O)(—O$^-$X)), $(C_1-C_{20})$alkylene-(C(=O)(—O$^-$X)), —$(C_1-C_{20})$alkyl, —H, or none;
$R^{10}$ is —$(C_1-C_6)$alkylene, or —H;
$R^{11}$ is side chain of amino acid such as methyl group (—CH$_3$), guanidino group (—(CH$_2$)$_3$—NH—C(=NH)—NH$_2$), amide group (—CH$_2$—CONH$_2$), (—CH$_2$—CH$_2$—CONH$_2$), carboxyl group (—CH$_2$—COOH), (—CH$_2$—CH$_2$—COOH), thiol group (—CH$_2$—SH), amide group (—CH$_2$—CH$_2$—CONH$_2$), carboxyl group (—CH$_2$—CH$_2$—COOH), hydrogen atom (—H), imidazole group (—CH$_2$—C$_3$H$_3$N2), sec-butyl group (—CH(CH$_3$)—CH$_2$—CH$_3$), isobutyl group (—CH$_2$—CH(CH$_3$)$_2$), amino group (—(CH$_2$)$_4$—NH$_2$), (—(CH$_2$)$_3$—NH$_2$), thioether group (—CH$_2$—CH$_2$—S—CH$_3$), hydroxymethyl group (—CH$_2$—OH), hydroxyethyl group (—CH(OH)—CH$_3$), hydroxyphenyl group (—CH$_2$—C$_6$H$_4$—OH), isopropyl group (—CH(CH$_3$)$_2$), or their derivative;
m is 0~150;
provided that if m>2, then Ar$^1$ or $R^{11}$ can be chosen independently;
Ar$^1$ is a substituted phenyl, an unsubstituted phenyl, a substituted indole, or an unsubstituted indole;
Ar$^2$ is a substituted phenyl, an unsubstituted phenyl, a substituted naphthyl, an unsubstituted naphthyl, a substituted indole, or an unsubstituted indole; and
X is H$^+$, Na$^+$, Ca$^+$, or K$^+$, and
wherein $R^{12}$, $R^{13}$, and $R^{14}$, each independently, represents the surface of the porous particle or an adjacent silane.

Embodiment 15. The method of one or more of Embodiments 14 and 15, wherein the active agent includes a kinase inhibitor selected from the group consisting of Abemaciclib, Abrocitinib, Acalabrutinib, Afatinib, Alectinib, Almonertinib, Alpelisib, Amivantamab, Apatinib, Asciminib, Avapritinib, Axitinib, Baricitinib, Binimetinib, Bosutinib, Brigatinib, Cabozantinib, Capivasertib, Capmatinib, Catequentinib, Ceritinib, Cetuximab, Cobimetinib, Copanlisib, Crizotinib, Dabrafenib, Dacomitinib, Dasatinib, Defactinib, Delgocitinib, Deucravacitinib, Duvelisib, Encorafenib, Entrectinib, Erdafitinib, Erlotinib, Everolimus, Fasudil, Fedratinib, Filgotinib, Flumatinib, Fostamatinib, Fostamatinib, Fruquintinib, Furmonertinib, Futibatinib, Gefitinib, Gilteritinib, Ibrutinib, Icotinib, Idelalisib, Imatinib, Infigratinib, Ivosidenib, Lapatinib, Larotrectinib, Lazertinib, Leniolisib, Lenvatinib, Lorlatinib, Margetuximab, Midostaurin, Mobocertinib, Necitumumab, Neratinib, Netarsudil, Nilotinib, Nimotuzumab, Nintedanib, Olaratumab, Olmutinib, Orelabrutinib, Osimertinib, Pacritinib, Palbociclib, Panitumumab, Paxalisib, Pazopanib, Peficitinib, Pemigatinib, Pertuzumab, Pexidartinib, Pirtobrutinib, Ponatinib, Pralsetinib, Pyrotinib, Quizartinib, Radotinib, Ramucirumab, Regorafenib, Ribociclib, Ripasudil, Ripretinib, Ritlecitinib, Ruxolitinib, Savolitinib, Selpercatinib, Selumetinib, Simotinib, Sirolimus, Sorafenib, Sotorasib, Sunitinib, Surufatinib, Temsirolimus, Tenalisib, Tepotinib, Tirabrutinib, Tirbanibulin, Tivozanib, Tofacitinib, Trametinib, Trastuzumab, Trilaciclib, Tucatinib, Umbralisib, Upadacitinib, Vandetanib, Vemurafenib, Volasertib, Zanubrutinib, and mixtures thereof; or wherein the medical disorder is selected from the group consisting of Atopic dermatitis, Mantle cell lymphoma, NSCLC with EGFR mutations, NSCLC with ALK translocations, Advanced mutation+ve NSCLC, Breast cancer, HR+ve, HER2-ve, NSCLC, Gastric cancer, NSCLC, Chronic myelogenous leukemia, PDGFR exon 18 mutation (incl D842V)+ve, Renal Cell Carcinoma, Rheumatoid arthritis, BRAF mutant melanoma, Chronic Myelogenous Leukemia, ALK-rearranged metastatic NSCLC, Medullary Thyroid Cancer, HR+ve and PI3K mutation breast cancer, MET mutation+ve NSCLC, EGFR colorectal cancer, Melanoma, breast cancer, Follicular lymphoma, NSCLC with Alkmutation, Skin cancer, NSCLC with EGFR mutations, Chronic Myelogenous Leukemia, Solid tumors, Psoriasis, CLL, SLL, FL, BRAF mutant melanoma, ROS1+ve NSCLC, solid tumors NTRK+ve, Advanced metastatic urothelial carcinoma, Pancreatic Cancer, Renel Cell Carcinoma, Cerebral Vasospasm PAH, myelofibrosis Rheumatoid arthritis, Chronic myelogenous leukemia, Autoimmune thrombocytopenia, Chronic immune thrombocytopenia, Metastatic colorectal cancer, Cholangiocarcinoma, Acute myeloid leukemia FLT3 mutant, Mantle cell lymphoma, chronic lymphocytic leukemia, Chronic Myelogenous Leukemia, Acute myeloid leukemia (AML), Breast Cancer, Solid tumours with NTRK fusions, Activated phosphoinositide 3-kinase delta syndrome (APDS), PASLI (p110 delta activating mutation causing senescent T cells), lymphadenopathy, immunodeficiency, Thyroid cancer (DTC) kidney cancer, ALK+ve met NSCLC, MHER2-positive breast cancer, Acute myeloid leukemia (FLT3 mutation-positive), NSCLC with EGFR mutations, HER2-positive breast cancer, Glaucoma (topical), Chronic Myelogenous Leukemia, cell carcinomas of the head and neck, Idiopathic pulmonary fibrosis, Soft tissue sarcoma, T790M+ve NSCLC, mantle cell lymphoma CLL, SLL, T790M+ve NSCLC, Myelofibrosis, Advanced (metastatic) breast cancer EGFR colorectal cancer, Malignant glioblastoma, Renal cancer, Rhematoid arthritis, Cholangiocarcinoma with FGFR2 fusionA, HER2-positive breast cancer, Tenosynovial giant cell tumor, Mantle Cell Lymphoma, Chronic Myelogenous Leukemia, ALL, Met RET fusion+ve NSCLC MTC, Breast cancer, Acute myeloid leukemia, Chronic Myelogenous Leukemia, MNSCLC colorectal cancer, Clorectal Cancer GIST, HCC, Advanced (metastatic) breast cancer HR+ve, HER2-ve, Glaucoma ocular hypertension, Advanced GIST Mastocytosis, Severe alopecia, Myelofibrosis, Adenocarcinoma, NSCLC, NSCLC, MTC, thyroid cancers, Neurofibromatosis type 1, Solid tumors, kidney Transplantation, Renal Cancer HCC, KRAS non-small-cell lung cancer, Renal Cancer, Imatinib resistant GIST, Advanced pancreatic NET, Advanced Renal Cell Carcinoma, PTCL, breast cancer, Metastatic NSCLC, Chronic myelogenous leukemia, Actinic keratosis, Advanced RCC, Rheumatoid arthritis, M-Melanoma with BRAFV600E, EGFR breast cancer, SCLC chemo myelo preservation, HER2-positive breast cancer, Marginal zone lymphoma, Rheumatoid arthritis, Thyroid Cancer, Metastatic Melanoma BRAFV600E, Acute myeloid leukemia, and mantle cell lymphoma; or wherein a cell in a target tissue is a cancer cell or a cell located within a tumor; or further comprising, releasing an active agent within a cell in a target tissue by passing the composition into an interior of the target tissue.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices, and materials are described herein. It is to be understood that this disclosure is not limited to particular methods, and experimental conditions described, as such methods and conditions can vary.

Without further elaboration, it is believed that one skilled in the art can, using the description herein, utilize the present invention to its fullest extent. The embodiments described herein are to be construed as illustrative and not as constraining the remainder of the disclosure in any way whatsoever. While the preferred embodiments of the invention have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

Production of Porous Silicon Particles:

For production of porous silicon particles, a heavily doped p++ type silicon wafer with a resistivity of 0.005 ohm-cm (Silicon Quest Inc., CA) is used. A first protective layer of silicon dioxide is deposited on the wafer. A second protective layer of photoresist is deposited on the first protective layer. The second protective layer is then patterned to form protected areas of the protective layer and non-protected areas. Etching (first etching) is performed on the non-protected areas of the first protective layer, by exposing the non-protected areas of the first protective layer to reactive ion etching under an atmosphere of $CF_4$ and $CHF_3$ to form first protective layer pillars.

Etching (second etching) is then performed by inductively coupled plasma reactive ion etching under the atmosphere of $SF_6$ to form silicon pillars. The second protective layer on the top of first protective layer pillars is then removed by using a piranha solution (1 volume $H_2O_2$ and 2 volumes $H_2SO_4$) and the fluorinated polymeric residual on sidewalls is cleaned in a solvent such as NMP (N-Methyl-2-pyrrolidone) or 3M® Novec™ 7200 Engineered Fluid (ethoxynonafluorobutane).

A dielectric layer of silicon nitride is then deposited over the first protective layer pillars, the silicon pillar sidewalls, and the silicon trenches. The tops of the pillars are then exposed by removing portions of the dielectric layer by RIE (reactive ion etching) under an atmosphere of $SF_6$. After such removal, the dielectric layer remains intact on the sides and at the bottom of the etched areas.

The first protective layer pillars are then removed by exposing the first protective layer pillars to an etching (fourth etching) solution comprising HF. After that, the nanopores (porous silicon pillars) are formed by electrochemical etching using a mixture of hydrofluoric acid (HF) and ethanol (1:3 v/v) with applied current density of about 20 mA/cm$^2$ to form a first porous layer, which is a stable porous layer from which the particles are formed. After that, a release high porosity layer, is formed by applying the current density of 120 mA/cm$^2$, which is a release porous layer with a larger porosity than the first porous layer.

The steps of formation of a stable porous layer and formation of a release layer are then repeated a number of times to form a periodical layered or stacked porous silicon structures defining a plurality of first porous layers (i.e., porous silicon structures) separated by second porous layers. SEM (scanning electron microscopy) images are used to confirm or characterize the shapes (flat or planar top and flat or planar bottom surfaces) and sizes of the porous silicon structures (particles). For more information on how the microparticles were or can be produced, see, e.g., PCT/US23/33524, published as WO/2024/064368.

Example 1 (Preparing FIG. 1)

Transfer the porous silicon particles suspension (14 mL) into a TEFLON® test tube. The porous silicon particles were spined down at 3000 rpm (rotations per minute) for 5 min, the supernatant (IPA, isopropyl alcohol) was discarded, then resuspend/vortex [sonicate if it is necessary]/spin down with toluene 10 mL for 2 times (toluene wash 2 times). The washed porous silicon particles were transferred with 13.2 mL of toluene into 100 mL round bottom flask equipped with Dimroth condenser, drying tube, and a TEFLON®-coated magnetic stirrer bar. APTES ((3-Aminopropyl)triethoxysilane) (0.84 mL) was added to the suspension and the reaction mixture was stirred for 5-10 seconds at ~1000 rpm. The reaction mixture was heated in the oil bath at 120° C. without stirring for 24 hours (occasionally agitate the reaction mixture with stirring, about 5 times in 24 hours reaction time). The reaction mixture was cooled down to room temperature and transfer the suspension to a TEFLON® test tube. The activated porous silicon particles were washed with 14 mL of ethanol four times. Ninhydrin test of the final washing solution was negative. The activated porous silicon particles were kept in ethanol (14 mL) in a refrigerator at 4° C. The amount of loading was estimated by ninhydrin assay.

The activated porous silicon particles suspension (1 mL, porous silicon particles 6.0 mg) was transferred into a TEFLON® test tube, and spined down at 3000 rpm for 5 min. The supernatant (ethanol) was discarded, then the porous silicon particles were resuspended/vortexed [sonicate if it is necessary]/spined down with DMF 1 mL for 3 times (DMF wash 3 times). Palmitic acid (53.8 mg) was placed in a round-bottomed flask and dissolved in DMF (Dimethylformamide) ((0.6 mL). To the solution was added DIC (N,N'-Diisopropylcarbodiimide) (16.4 µL), and the reaction mixture was stirred for five minutes at room temperature. The reaction mixture was transferred to the TEFLON® test tube containing activated porous silicon particles, and DIPEA (N,N-Diisopropylethylamine) (22.8 µL) was added to the mixture. The reaction mixture was agitated on the orbital shaker at 180 rpm for 21 hours at room temperature. The modified porous silicon particles were washed with DMSO (Dimethyl sulfoxide) (2 mL) three times and with methanol three times and dried under the vacuum for 3 hours to obtain the product (porous silicon particles-ex1). The amount of loading was estimated by ninhydrin assay.

The dry porous silicon particles-ex1 (3 mg) were treated with a solution of dasatinib (0.4 mL) in phosphate buffer (0.5 mg/mL) with vertex and sonication. The uniformed suspension was agitated by an orbital shaker (200 rpm) for 12 hours. The suspension was spined down and the supernatant was removed to give the product. The loading efficiency was evaluated by Ultraviolet-visible (UV-vis) spectroscopy quantification of the residual dasatinib in the supernatant, loading efficiency; 81%, loading capacity; 5.4%.

Example 2 (Preparing FIG. 2)

The activated porous silicon particles suspension (15 mL, porous silicon particles 72 mg) was transferred into a TEFLON® test tube, and spined down at 3000 rpm for 5 min. The supernatant (ethanol) was discarded, then porous silicon particles were resuspended/vortexed [sonicate if it is necessary]/spined down with methanol 10 mL, and the supernatant was discarded. The porous silicon particles were dried under vacuum for 3 hrs. To the dried porous silicon particles, a solution of eicosanedioic acid (201 mg) in DMSO (14 mL) and DIPEA (208 L) were added. The suspension was agitated by vortex and sonication. To the reaction mixture was added a solution of HBTU (Hexafluorophosphate Benzotriazole Tetramethyl Uronium) (224 mg) in DMSO (0.7 mL). The reaction mixture was agitated on the orbital shaker at 180 rpm for 15 hours at room temperature and stood for an hour at 60° C. The porous silicon particles were spined down at 3000 rpm for 5 min, the supernatant was discarded. A solution of eicosanedioic acid (201 mg) and DIPEA (208 µL) in DMSO (14 mL), and a solution of HBTU (224 mg) in DMSO (0.7 mL) were added to the suspension of porous silicon particles. The reaction mixture was agitated on the orbital shaker at 180 rpm for 3 hours at room temperature. The modified porous silicon particles were washed with DMSO (10 mL) two times and with methanol (10 mL) two times. The porous silicon particles were treated with 10% water in pyridine (3.3 mL) for 3 hours at room temperature. The porous silicon particles were washed with methanol (10 mL) twice, then treated with 5% TFA in chloroform (3 mL) for 10 minutes. The porous silicon particles were then washed with methanol (10 mL) twice and dried under the vacuum for 3 hours to obtain the product (porous silicon particles-ex2). The amount of loading was estimated by ninhydrin assay.

The dry porous silicon particles-ex2 (700 g) were treated with a solution of dasatinib (10 mL) in water (6 g/mL) with vertex and sonication. The uniformed suspension was agitated by an orbital mixer (200 rpm) for 3 hours. The suspension was spined down and the supernatant was removed to give the product. The loading efficiency was evaluated by UV-vis spectroscopy quantification of the residual dasatinib in the supernatant, loading efficiency; 57%, loading capacity; 5.0%. For the estimation of release kinetics of dasatinib, the complex of silicon particle-ex2 and dasatinib was treated with phosphorus buffer (pH=7.4) and citric acid buffer (pH 5.2) separatory. The concentration of gefitinib was quantified by LC-MS. See FIG. 6 and FIG. 7 for release kinetics data.

The dry porous silicon particles-ex2 (248 g) were treated with a solution of gefitinib (1.0 mL) in water (15 g/mL) with vertex and sonication. The uniformed suspension was agitated by an orbital shaker (200 rpm) for 3 hours. The suspension was spined down and the supernatant was removed to give the product. The loading efficiency was evaluated by LC-MS quantification of the residual gefitinib in the supernatant, loading efficiency; 60%, loading capacity; 3.6%. For the estimation of release kinetics of gefitinib, the complex of silicon particle-ex2 and gefitinib was treated with phosphorus buffer (pH=7.4) and citric acid buffer (pH 5.2) separatory. The concentration of gefitinib was quantified by LC-MS. See FIG. 8 for release kinetics data.

Example 3 (Preparing FIG. 3)

The activated porous silicon particles suspension (3 mL, porous silicon particles 6.96 mg) was transferred into a TEFLON® test tube and spined down at 3000 rpm for 5 min. The supernatant (ethanol) was discarded, then the porous silicon particles were resuspended/vortexed [sonicate if it is necessary]/spined down with methanol 10 mL, and the supernatant was discarded. The porous silicon particles were dried under vacuum for 3 hrs. To the dried porous silicon particles, a solution of Fmoc-Phe (N-(9-Fluorenylmethoxycarbonyl)-L-phenylalanine) (28.9 mg) and HBTU (29.4 mg) in DMF (0.6 mL) and DIPEA (19.5 µL) were added. The suspension was agitated by vortex and sonication. The reaction mixture was agitated on the orbital shaker at 180 rpm for 15 hours at room temperature and stood for an hour at 60° C. The porous silicon particles were spin down at 3000 rpm for 5 min, the supernatant was discarded. A solution of Fmoc-Phe (28.9 mg) and HBTU (29.4 mg) in DMF (0.6 mL) and DIPEA (19.5 µL) were added to the porous silicon particles. The reaction mixture was agitated on the orbital shaker at 180 rpm for 15 hours at room temperature. The modified porous silicon particles were washed with DMF (2.5 mL) two times and with methanol (2.5 mL) two times. The porous silicon particles were dried under vacuum for 3 hours to obtain 5.8 mg of the product (porous silicon particles-FmocPhe). The amount of loading was estimated by ninhydrin assay.

The porous silicon particles-FmocPhe (5.8 mg) was treated with 20% piperidine in DMF (1 ml) for 30 minutes at room temperature. The product was washed with DMF (3 mL) for 3 times and with methanol (3 mL) for 3 times. The porous silicon particles were dried under vacuum for 3 hours to obtain 5.8 mg of the product (porous silicon particles-Phe).

To the dried porous silicon particles-Phe (2.4 mg) in TEFLON® test tube, a solution of octanedioic acid (9.3 mg) in DMSO (0.6 mL) and DIPEA (13.9 µL) were added. The suspension was agitated by vortex and sonication. To the reaction mixture was added a solution of HBTU (20.2 mg) in DMSO (0.2 mL). The reaction mixture was agitated on the orbital shaker at 180 rpm for 15 hours at room temperature and stood for an hour at 60° C. The porous silicon particles were spined down at 3000 rpm for 5 min, and the supernatant was discarded. A solution of octanedioic acid (9.3 mg) in DMSO (0.6 mL) and DIPEA (13.9 µL) followed by a solution of HBTU (20.2 mg) in DMSO (0.2 mL) were added to the porous silicon particles. The suspension was agitated by vortex and sonication. The reaction mixture was agitated on the orbital shaker at 180 rpm for 15 hours at room temperature. The modified porous silicon particles were washed with DMSO (2.5 mL) two times and with methanol (2.5 mL) two times. The porous silicon particles were treated with 10% water in pyridine (0.55 mL) for 3 hours at room temperature. The porous silicon particles were washed with methanol (3 mL) twice, then treated with 5% TFA (Trifluoroacetic acid) in chloroform (0.5 mL) for 10 minutes. The porous silicon particles were washed with methanol (3 mL) twice. The porous silicon particles were dried under vacuum for 3 hours to obtain 1.9 mg of the product (porous silicon particles-ex3).

Figure 10:
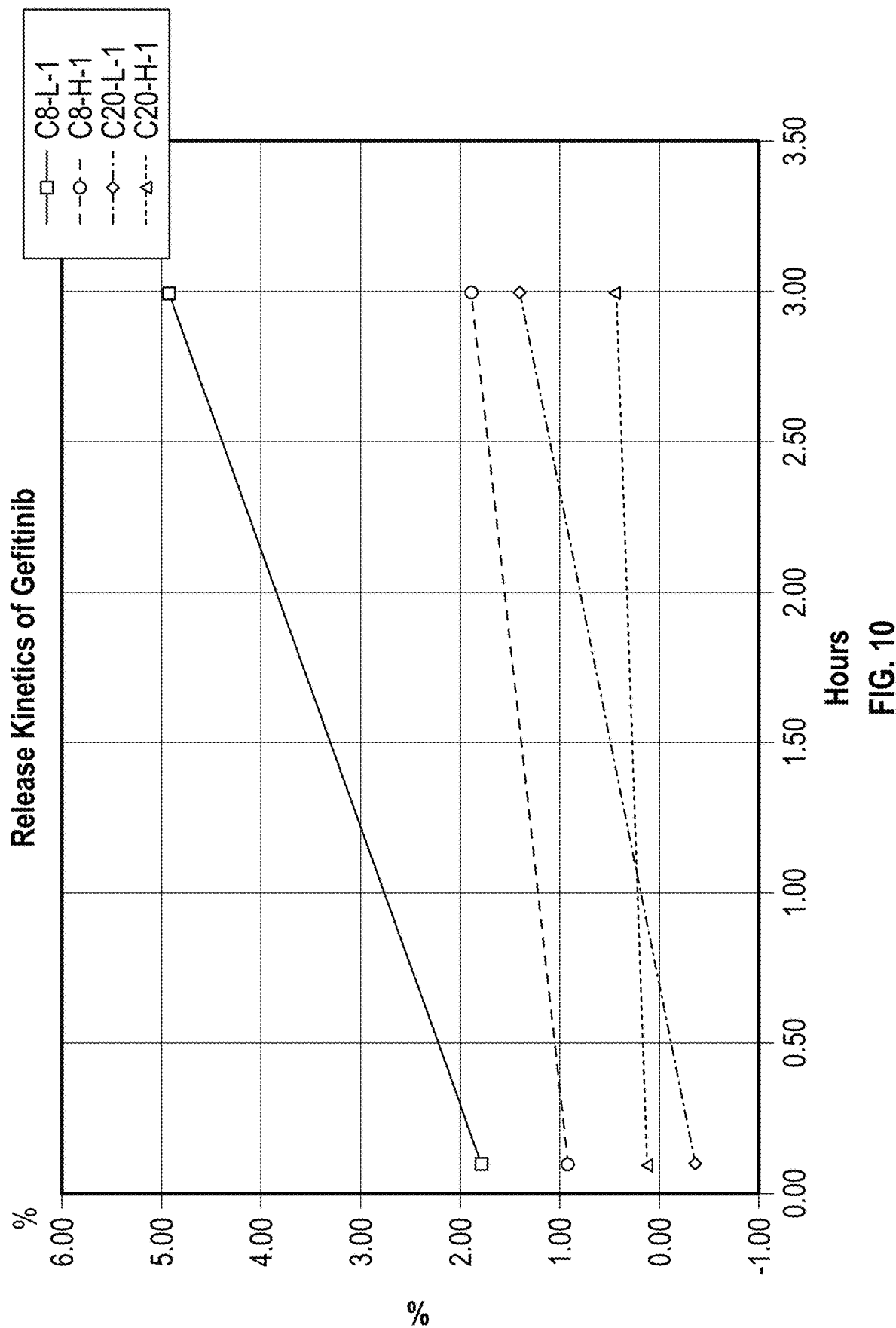
FIG. 10 is a graph showing release kinetics of gefitinib from an embodiment of a composition according to the present disclosure in buffer solution.

The dry porous silicon particles-ex3 (C-8) (216 g) were treated with a solution of gefitinib (1.44 mL) in water (15 g/mL) with vertex and sonication. The uniformed suspension was agitated by an orbital shaker (200 rpm) for 3 hours. The suspension was spined down and the supernatant was removed to give the product. The loading efficiency was evaluated by LC-MS quantification of the residual gefitinib in the supernatant, loading efficiency; 87%, loading capacity; 8.7%. For the estimation of release kinetics of gefitinib, the complex of silicon particle-ex3 and gefitinib was treated with phosphorus buffer (pH=7.4) (H-1) and citric acid buffer (pH 5.2) (L-1) separatory. The concentration of gefitinib was quantified by LC-MS. See FIG. 10 for release kinetics data.

Example 5 (Preparing FIG. 5)

To the dried porous silicon particles-Phe (2.9 mg) in TEFLON® test tube, a solution of eicosanedioic acid (18.3 mg) in DMSO (0.6 mL) and DIPEA (13.9 µL) were added. The suspension was agitated by vortex and sonication. To the reaction mixture was added a solution of HBTU (20.2 mg) in DMSO (0.2 mL). The reaction mixture was agitated on the orbital shaker at 180 rpm for 15 hours at room temperature and stood for an hour at 60° C. The porous silicon particles were spined down at 3000 rpm for 5 min, the supernatant was discarded. A solution of eicosanedioic acid (18.3 mg) in DMSO (0.6 mL) and DIPEA (13.9 µL) followed by a solution of HBTU (20.2 mg) in DMSO (0.2 mL) were added to the porous silicon particles. The suspension was agitated by vortex and sonication. The reaction mixture was agitated on the orbital shaker at 180 rpm for 15 hours at room temperature. The modified porous silicon particles were washed with DMSO (2.5 mL) two times and with methanol (2.5 mL) two times. The porous silicon particles were treated with 10% water in pyridine (0.55 mL) for 3 hours at room temperature. The porous silicon particles were washed with methanol (3 mL) twice, then treated with 5% TFA in chloroform (0.5 mL) for 10 minutes. The porous silicon particles were washed with methanol (3 mL) twice. The porous silicon particles were dried under vacuum for 3 hours to obtain 3.0 mg of the product (porous silicon particles-ex5).

The dry porous silicon particles-ex5 (133 g) were treated with a solution of gefitinib (0.887 mL) in water (15 g/mL) with vertex and sonication. The uniformed suspension was agitated by an orbital shaker (200 rpm) for 3 hours. The suspension was spined down and the supernatant was removed to give the product. The loading efficiency was evaluated by LC-MS quantification of the residual gefitinib in the supernatant, loading efficiency; 92%, loading capacity; 9.2%. For the estimation of release kinetics of gefitinib, the complex of silicon particle-ex5 (C-20) and gefitinib was treated with phosphorus buffer (pH=7.4) (H-1) and citric acid buffer (pH 5.2) (L-1) separatory. The concentration of gefitinib was quantified by LC-MS. See FIG. 10 for release kinetics data.

What is claimed is:

1. A composition for delivery of an active agent to a cell in a target tissue of a subject in need thereof, comprising:
an active agent; and
a porous particle, wherein the porous particle comprises a plurality of microscale reservoirs and a host molecular structure is adhered to a surface of the porous particle, wherein the host molecular structure has a structure of Formula 1,
wherein:

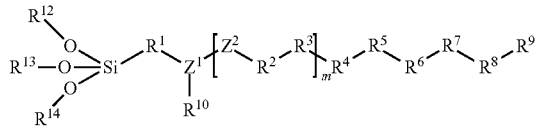

Formula 1

$R^1$ is —($C_1$-$C_6$)alkylene-, or —H;
$Z^1$ is —(N—)—, —H, or none;
$Z^2$ is —(C(=O))—, —$SO_2$—, or none;
$R^2$ is —(C(—H)—$R^{11}$)—, —($C_1$-$C_3$)alkylene, —(C(—H)—(($C_1$-$C_6$)alkylene-(C(=O) (—O⁻X))))—, (C(—H)(—($C_1$-$C_6$)alkylene-$Ar^1$)), —O—, —H, or none;
$R^3$ is —($CH_2$)—, —(N(—H))—, —H, or none;
$R^4$ is —($CH_2$)—, —(C(=O))—, —H, or none;
$R^5$ is —($C_1$-$C_{20}$)alkylene-, —($C_1$-$C_3$)alkylene-$Ar^2$, —O—, —H, or none;
$R^6$ is —($CH_2$)—, —H, or none;
$R^7$ is —($CH_2$)—, —(C(=O))—, —H, or none;
$R^8$ is —($CH_2$)—, —(N(—H))—, —H, or none;
$R^9$ is —($C_1$-$C_3$)alkylene-$Ar^2$, —(C(=O)(—O⁻X)), ($C_1$-$C_{20}$)alkylene-(C(=O)(—O⁻X)), —($C_1$-$C_{20}$)alkyl, —H, or none;
$R^{10}$ is —($C_1$-$C_6$)alkyl, or —H;
$R^{11}$ is side chain of amino acid selected from the group consisting of methyl group (—$CH_3$), guanidino group (—($CH_2$)$_3$—NH—C(=NH)—$NH_2$), amide group (—$CH_2$—$CONH_2$), (—$CH_2$—$CH_2$—$CONH_2$), carboxyl group (—$CH_2$—COOH), (—$CH_2$—$CH_2$—COOH), thiol group (—$CH_2$—SH), amide group (—$CH_2$—$CH_2$—$CONH_2$), carboxyl group (—$CH_2$—$CH_2$—COOH), hydrogen atom (—H), imidazole group (—$CH_2$—$C_3H_3N_2$), sec-butyl group (—CH($CH_3$)—$CH_2$—$CH_3$), isobutyl group (—$CH_2$—CH($CH_3$)$_2$), amino group (—($CH_2$)$_4$—$NH_2$), (—($CH_2$)$_3$—$NH_2$), thioether group (—$CH_2$—$CH_2$—S—$CH_3$), hydroxymethyl group (—$CH_2$—OH), hydroxyethyl group (—CH(OH)—$CH_3$), hydroxyphenyl group (—$CH_2$—$C_6H_4$—OH), and isopropyl group (—CH($CH_3$)$_2$);
m is 0~150;
provided that if m>2, then $Ar^1$ or $R^{11}$ can be chosen independently;
$Ar^1$ is a substituted phenyl, an unsubstituted phenyl, a substituted indole, or an unsubstituted indole;
$Ar^2$ is a substituted phenyl, an unsubstituted phenyl, a substituted naphthyl, an unsubstituted naphthyl, a substituted indole, or an unsubstituted indole; and
X is H⁺, Na⁺, Ca⁺, or K⁺, and
$R^{12}$, $R^{13}$, and $R^{14}$, each independently, represents the surface of the porous particle or an adjacent silane.

2. The composition of claim 1, wherein:
$Z^1$ is —(N—)—;
$Z^2$ is —(C(=O))—;
$R^2$ is —(C(—H)(—($C_1$-$C_6$)alkylene-$Ar^1$)) and $Ar^1$ is an unsubstituted phenyl;
$R^3$ is —(N(—H))—;
$R^4$ is —(C(=O))—;
$R^9$ is —($C_1$-$C_{20}$)alkylene-(C(=O)(—O⁻X)); and
$R^{10}$ is —H.

3. The composition of claim 1, wherein:
$Z^1$ is —(N—)—;
$Z^2$ is —(C(=O))—;
$R^2$ is —(C(—H)—(($C_1$-$C_6$)alkylene-(C(=O)(—O⁻X))));
$R^3$ is —(N(—H))—;
$R^4$ is —(C(=O))—;
$R^7$ is —(C(=O))—;
$R^9$ is —($C_1$-$C_3$)alkylene-$Ar^2$ and $Ar^2$ is an unsubstituted phenyl; and
$R^{10}$ is —H.

4. The composition of claim 1, wherein:
$Z^1$ is —(N—)—;
$Z^2$ is —(C(=O))—;
$R^9$ is —($C_1$-$C_3$)alkylene-$Ar^2$, —(C(=O)(—O⁻X)), ($C_1$-$C_{20}$)alkylene-(C(=O)(—O⁻X)), or ($C_1$-$C_{20}$)alkyl; and
$R^{10}$ is —H.

5. The composition of claim 1, wherein the host molecular structure has a structure of Formula 2, Formula 3, Formula 4, or Formula 5, or mixture thereof:

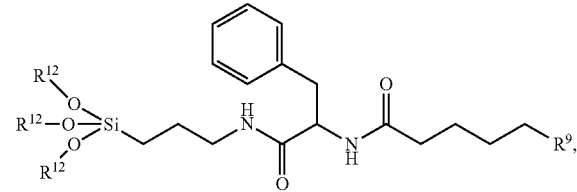

Formula 2 wherein $R^9$ is —($C_1$-$C_{20}$)alkylene-(C(=O)(—O⁻X));

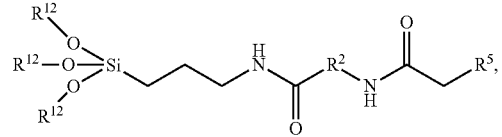

Formula 3

$R^2$ is —(C(—H)—((C$_1$-C$_6$)alkylene-(C(=O)(—O$^-$X))))
and $R^5$ is —(C$_1$-C$_3$)alkylene-Ar$^2$;

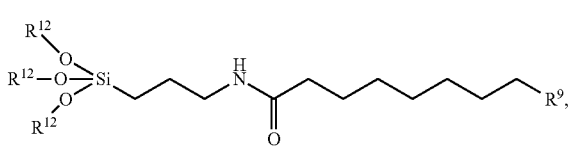

Formula 4 wherein $R^9$ is —(C$_1$-C$_{20}$)alkyl; and

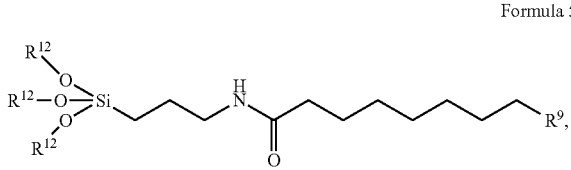

Formula 5 wherein $R^9$ is —(C$_1$-C$_{20}$)alkylene-(C(=O)(—O$^-$X));
wherein $R^{12}$, $R^{13}$, and $R^{14}$, each independently, represents the surface of the porous particle or an adjacent silane.

6. The composition of claim 1, wherein the porous particle is a micro or a nano particle; or
wherein the porous particle is biocompatible and degradable; or
wherein the plurality of microscale reservoirs of the porous particle has a size ranging from about 0.3 µm to about 4 µm; or
wherein the porous particle has a shape selected from the group consisting of discoidal, spheroid, non-spheroid, oblate spheroid, and combinations thereof; or
wherein the porous particle includes a porous oxide material or a porous etched material; or
wherein the porous particle is able to overcome at least one biological barrier; or any combination thereof.

7. The composition of claim 1, wherein the porous particle includes a porous oxide material selected from the group consisting of porous silica, porous aluminum oxide, porous titanium oxide, porous iron oxide, and combinations thereof, or
wherein the porous particle includes a porous etched material selected from the group consisting of porous silicon, porous silica, porous germanium, porous GaAs, porous InP, porous SiC, porous Si$_x$Ge$_{1-x}$, porous GaP, porous GaN, and combinations thereof.

8. The composition of claim 1, wherein the active agent includes a kinase inhibitor; or
wherein the surface of the porous particle includes an interior surface of a pore of the porous particle; or
wherein the active agent is retained for a longer duration at a retention pH by a porous particle having the molecular host structure than a porous particle that excludes the molecular host structure; or
wherein the active agent forms a non-covalent complex with the molecular host structure.

9. The composition of claim 1, wherein the active agent includes a kinase inhibitor selected from the group consisting of Abemaciclib, Abrocitinib, Acalabrutinib, Afatinib, Alectinib, Almonertinib, Alpelisib, Amivantamab, Apatinib, Asciminib, Avapritinib, Axitinib, Baricitinib, Binimetinib, Bosutinib, Brigatinib, Cabozantinib, Capivasertib, Capmatinib, Catequentinib, Ceritinib, Cetuximab, Cobimetinib, Copanlisib, Crizotinib, Dabrafenib, Dacomitinib, Dasatinib, Defactinib, Delgocitinib, Deucravacitinib, Duvelisib, Encorafenib, Entrectinib, Erdafitinib, Erlotinib, Everolimus, Fasudil, Fedratinib, Filgotinib, Flumatinib, Fostamatinib, Fostamatinib, Fruquintinib, Furmonertinib, Futibatinib, Gefitinib, Gilteritinib, Ibrutinib, Icotinib, Idelalisib, Imatinib, Infigratinib, Ivosidenib, Lapatinib, Larotrectinib, Lazertinib, Leniolisib, Lenvatinib, Lorlatinib, Margetuximab, Midostaurin, Mobocertinib, Necitumumab, Neratinib, Netarsudil, Nilotinib, Nimotuzumab, Nintedanib, Olaratumab, Olmutinib, Orelabrutinib, Osimertinib, Pacritinib, Palbociclib, Panitumumab, Paxalisib, Pazopanib, Peficitinib, Pemigatinib, Pertuzumab, Pexidartinib, Pirtobrutinib, Ponatinib, Pralsetinib, Pyrotinib, Quizartinib, Radotinib, Ramucirumab, Regorafenib, Ribociclib, Ripasudil, Ripretinib, Ritlecitinib, Ruxolitinib, Savolitinib, Selpercatinib, Selumetinib, Simotinib, Sirolimus, Sorafenib, Sotorasib, Sunitinib, Surufatinib, Temsirolimus, Tenalisib, Tepotinib, Tirabrutinib, Tirbanibulin, Tivozanib, Tofacitinib, Trametinib, Trastuzumab, Trilaciclib, Tucatinib, Umbralisib, Upadacitinib, Vandetanib, Vemurafenib, Volasertib, Zanubrutinib, and mixtures thereof.

10. A method of synthesizing a composition for delivery of an active agent to a cell in a target tissue of a subject in need thereof, comprising:
providing a porous particle, wherein the porous particle comprises a plurality of microscale reservoirs and a host molecular structure is adhered to a surface of the porous particle,
wherein the host molecular structure has a structure of Formula 1,
wherein:

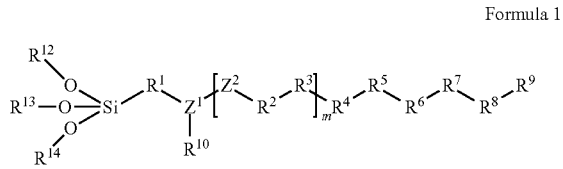

Formula 1

$R^1$ is (C$_1$-C$_6$)alkylene-, or —H;
$Z^1$ is —(N—)—, —H, or none;
$Z^2$ is —CO—, —SO$_2$—, or none;
$R^2$ is —(C(—H)—R$^{11}$)—, —(C$_1$-C$_3$)alkylene, —(C(—H)—((C$_1$-C$_6$)alkylene-(C(=O) (—O$^-$X))))—, —(C(—H)(—(C$_1$-C$_6$)alkylene-Ar$^1$)), —O—, —H, or none;
$R^3$ is —(CH$_2$)—, —(N(—H))—, —H, or none;
$R^4$ is —(CH$_2$)—, —(C(=O))—, —H, or none;
$R^5$ is —(C$_1$-C$_{20}$)alkylene-, —(C$_1$-C$_3$)alkylene-Ar$^2$, —O—, —H, or none;
$R^6$ is —(CH$_2$)—, —H, or none;
$R^7$ is —(CH$_2$)—, —(C(=O))—, —H, or none;
$R^8$ is —(CH$_2$)—, —(N(—H))—, —H, or none;
$R^9$ is —(C$_1$-C$_3$)alkylene-Ar$^2$, —(C(=O)(—O$^-$X)), (C$_1$-C$_{20}$)alkylene-(C(=O)(—O$^-$X)), —(C$_1$-C$_{20}$)alkyl, —H, or none;
$R^{10}$ is —(C$_1$-C$_6$)alkylene, or —H;
$R^{11}$ is side chain of amino acid selected from the group consisting of methyl group (—CH$_3$), guanidino group (—(CH$_2$)$_3$—NH—C(=NH)—NH$_2$), amide group (—CH$_2$—CONH$_2$), (—CH$_2$—CH$_2$—CONH$_2$), carboxyl group (—CH$_2$—COOH), (—CH$_2$—CH$_2$—COOH), thiol group (—CH$_2$—SH), amide group (—CH$_2$—CH$_2$—CONH$_2$), carboxyl group (—CH$_2$—

CH₂—COOH), hydrogen atom (—H), imidazole group (—CH₂—C₃H₃N2), sec-butyl group (—CH(CH₃)—CH₂—CH₃), isobutyl group (—CH₂—CH(CH₃)₂), amino group (—(CH₂)₄—NH₂), (—(CH₂)₃—NH₂), thioether group (—CH₂—CH₂—S—CH₃), hydroxymethyl group (—CH₂—OH), hydroxyethyl group (—CH(OH)—CH₃), hydroxyphenyl group (—CH₂—C₆H₄—OH), and isopropyl group (—CH(CH₃)₂), or their derivative;

m is 0~150;

provided that if m>2, then $Ar^1$ or $R^{11}$ can be chosen independently;

$Ar^1$ is a substituted phenyl, an unsubstituted phenyl, a substituted indole, or an unsubstituted indole;

$Ar^2$ is a substituted phenyl, an unsubstituted phenyl, a substituted naphthyl, an unsubstituted naphthyl, a substituted indole, or an unsubstituted indole; and X is $H^+$, $Na^+$, $Ca^+$, or $K^+$, and wherein $R^{12}$ represents the surface of the porous particle or an adjacent silane or a $(C_1-C_3)$alkyl;

wherein $R^{13}$ represents the surface of the porous particle or an adjacent silane;

wherein $R^{14}$ represents the surface of the porous particle or an adjacent silane;

providing an active agent; and mixing the active agent with the porous particle in a liquid medium.

11. The method of claim 10, further comprising:

providing the host molecular structure of Formula 1 by reacting a molecular structure of Formula 6 with a molecule of Formula 7, wherein

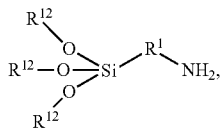

Formula 6

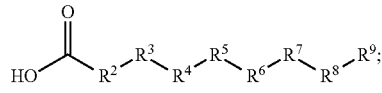

Formula 7 providing the host molecular structure having a structure of Formula 1 by reacting a molecule of Formula 8 with the surface of the porous particle,

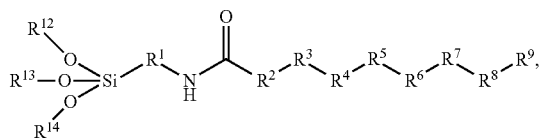

Formula 8 wherein $R^{12}$ is a $(C_1-C_3)$alkyl.

12. The method of claim 11, wherein providing the host molecular structure of Formula 1 by reacting a molecular structure of Formula 6 with a molecule of Formula 7 is performed in the presence of a carbodiimide or another peptide coupling reagent.

13. The method of claim 10, wherein the active agent includes a kinase inhibitor selected from the group consisting of Abemaciclib, Abrocitinib, Acalabrutinib, Afatinib, Alectinib, Almonertinib, Alpelisib, Amivantamab, Apatinib, Asciminib, Avapritinib, Axitinib, Baricitinib, Binimetinib, Bosutinib, Brigatinib, Cabozantinib, Capivasertib, Capmatinib, Catequentinib, Ceritinib, Cetuximab, Cobimetinib, Copanlisib, Crizotinib, Dabrafenib, Dacomitinib, Dasatinib, Defactinib, Delgocitinib, Deucravacitinib, Duvelisib, Encorafenib, Entrectinib, Erdafitinib, Erlotinib, Everolimus, Fasudil, Fedratinib, Filgotinib, Flumatinib, Fostamatinib, Fostamatinib, Fruquintinib, Furmonertinib, Futibatinib, Gefitinib, Gilteritinib, Ibrutinib, Icotinib, Idelalisib, Imatinib, Infigratinib, Ivosidenib, Lapatinib, Larotrectinib, Lazertinib, Leniolisib, Lenvatinib, Lorlatinib, Margetuximab, Midostaurin, Mobocertinib, Necitumumab, Neratinib, Netarsudil, Nilotinib, Nimotuzumab, Nintedanib, Olaratumab, Olmutinib, Orelabrutinib, Osimertinib, Pacritinib, Palbociclib, Panitumumab, Paxalisib, Pazopanib, Peficitinib, Pemigatinib, Pertuzumab, Pexidartinib, Pirtobrutinib, Ponatinib, Pralsetinib, Pyrotinib, Quizartinib, Radotinib, Ramucirumab, Regorafenib, Ribociclib, Ripasudil, Ripretinib, Ritlecitinib, Ruxolitinib, Savolitinib, Selpercatinib, Selumetinib, Simotinib, Sirolimus, Sorafenib, Sotorasib, Sunitinib, Surufatinib, Temsirolimus, Tenalisib, Tepotinib, Tirabrutinib, Tirbanibulin, Tivozanib, Tofacitinib, Trametinib, Trastuzumab, Trilaciclib, Tucatinib, Umbralisib, Upadacitinib, Vandetanib, Vemurafenib, Volasertib, or Zanubrutinib, or mixtures thereof; or wherein a weight percentage of about 1.0 wt % to about 10.0 wt % of the active agent is mixed with the porous particle in a liquid medium, based on a total weight of the composition in the liquid medium; or wherein the liquid medium includes water, methanol, ethanol, propanol, dimethylsulfoxide (DMSO), or a mixture thereof.

14. A method of treating a medical disorder in a subject in need thereof, comprising:

administering to the subject in need thereof a composition, wherein the composition includes an active agent; and a porous particle, wherein the porous particle comprises a plurality of microscale reservoirs and a host molecular structure is adhered to a surface of the porous particle, wherein the host molecular structure has a structure of Formula 1, wherein:

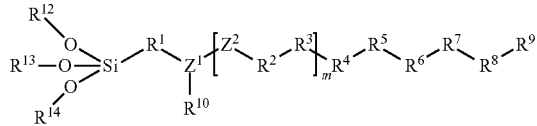

Formula 1

$R^1$ is —$(C_1-C_6)$alkylene-, or —H;

$Z^1$ is —(N—)—, —H, or none;

$Z^2$ is —CO—, $SO_2$, or none;

$R^2$ is —(C(—H)—$R^{11}$)—, —$(C_1-C_3)$alkylene, —(C(—H)—(($C_1-C_6$)alkylene-(C(═O)(—O⁻X))))—, —(C(—H)(—$(C_1-C_6)$alkylene-$Ar^1$))—, —O—, —H, or none;

$R^3$ is —(CH₂)—, —(N(—H))—, —H, or none;

$R^4$ is —(CH₂)—, —(C(═O))—, —H, or none;

$R^5$ is —$(C_1-C_{20})$alkylene, —$(C_1-C_3)$alkylene-$Ar^2$, —O—, —H, or none;

$R^6$ is —(CH₂)—, —H, or none;

$R^7$ is —(CH₂)—, —(C(═O))—, —H, or none;

$R^8$ is —(CH₂)—, —(N(—H))—, —H, or none;

R⁹ is —(C₁-C₃)alkylene-Ar², —(C(=O)(—O⁻X)), (C₁-C₂₀)alkylene-(C(=O)(—O⁻X)), —(C₁-C₂₀)alkyl, —H, or none;

R¹⁰ is —(C₁-C₆)alkylene, or —H;

R¹¹ is side chain of amino acid selected from the group consisting of methyl group (—CH₃), guanidino group (—(CH₂)₃—NH—C(=NH)—NH₂), amide group (—CH₂—CONH₂), (—CH₂—CH₂—CONH₂), carboxyl group (—CH₂—COOH), (—CH₂—CH₂—COOH), thiol group (—CH₂—SH), amide group (—CH₂—CH₂—CONH₂), carboxyl group (—CH₂—CH₂—COOH), hydrogen atom (—H), imidazole group (—CH₂—C₃H₃N₂), sec-butyl group (—CH(CH₃)—CH₂—CH₃), isobutyl group (—CH₂—CH(CH₃)₂), amino group (—(CH₂)₄—NH₂), (—(CH₂)₃—NH₂), thioether group (—CH₂—CH₂—S—CH₃), hydroxymethyl group (—CH₂—OH), hydroxyethyl group (—CH(OH)—CH₃), hydroxyphenyl group (—CH₂—C₆H₄—OH), and isopropyl group (—CH(CH₃)₂);

m is 0~150;

provided that if m>2, then Ar¹ or R¹¹ can be chosen independently;

Ar¹ is a substituted phenyl, an unsubstituted phenyl, a substituted indole, or an unsubstituted indole;

Ar² is a substituted phenyl, an unsubstituted phenyl, a substituted naphthyl, an unsubstituted naphthyl, a substituted indole, or an unsubstituted indole; and X is H⁺, Na⁺, Ca⁺, or K⁺, and wherein R¹², R¹³, and R¹⁴, each independently, represents the surface of the porous particle or an adjacent silane.

15. The method of claim 14, wherein the active agent includes a kinase inhibitor selected from the group consisting of Abemaciclib, Abrocitinib, Acalabrutinib, Afatinib, Alectinib, Almonertinib, Alpelisib, Amivantamab, Apatinib, Asciminib, Avapritinib, Axitinib, Baricitinib, Binimetinib, Bosutinib, Brigatinib, Cabozantinib, Capivasertib, Capmatinib, Catequentinib, Ceritinib, Cetuximab, Cobimetinib, Copanlisib, Crizotinib, Dabrafenib, Dacomitinib, Dasatinib, Defactinib, Delgocitinib, Deucravacitinib, Duvelisib, Encorafenib, Entrectinib, Erdafitinib, Erlotinib, Everolimus, Fasudil, Fedratinib, Filgotinib, Flumatinib, Fostamatinib, Fostamatinib, Fruquintinib, Furmonertinib, Futibatinib, Gefitinib, Gilteritinib, Ibrutinib, Icotinib, Idelalisib, Imatinib, Infigratinib, Ivosidenib, Lapatinib, Larotrectinib, Lazertinib, Leniolisib, Lenvatinib, Lorlatinib, Margetuximab, Midostaurin, Mobocertinib, Necitumumab, Neratinib, Netarsudil, Nilotinib, Nimotuzumab, Nintedanib, Olaratumab, Olmutinib, Orelabrutinib, Osimertinib, Pacritinib, Palbociclib, Panitumumab, Paxalisib, Pazopanib, Peficitinib, Pemigatinib, Pertuzumab, Pexidartinib, Pirtobrutinib, Ponatinib, Pralsetinib, Pyrotinib, Quizartinib, Radotinib, Ramucirumab, Regorafenib, Ribociclib, Ripasudil, Ripretinib, Ritlecitinib, Ruxolitinib, Savolitinib, Selpercatinib, Selumetinib, Simotinib, Sirolimus, Sorafenib, Sotorasib, Sunitinib, Surufatinib, Temsirolimus, Tenalisib, Tepotinib, Tirabrutinib, Tirbanibulin, Tivozanib, Tofacitinib, Trametinib, Trastuzumab, Trilaciclib, Tucatinib, Umbralisib, Upadacitinib, Vandetanib, Vemurafenib, Volasertib, or Zanubrutinib, or mixtures thereof, or wherein the medical disorder is selected from the group consisting of Atopic dermatitis, Mantle cell lymphoma, NSCLC with EGFR mutations, NSCLC with ALK translocations, Advanced mutation+ve NSCLC, Breast cancer, HR+ve, HER2-ve, NSCLC, Gastric cancer, NSCLC, Chronic myelogenous leukemia, PDGFR exon 18 mutation (D842V)+ve, Renal Cell Carcinoma, Rheumatoid arthritis, BRAF mutant melanoma, Chronic Myelogenous Leukemia, ALK-rearranged metastatic NSCLC, Medullary Thyroid Cancer, HR+ and PI3K mutation breast cancer, MET mutation+ve NSCLC, EGFR colorectal cancer, Melanoma, breast cancer, Follicular lymphoma, NSCLC with Alkmutation, Skin cancer, NSCLC with EGFR mutations, Chronic Myelogenous Leukemia, Solid tumors, Psoriasis, CLL, SLL, FL, BRAF mutant melanoma, ROS1+ve NSCLC, solid tumors NTRK+ve, Advanced metastatic urothelial carcinoma, Pancreatic Cancer, Renel Cell Carcinoma, Cerebral Vasospasm PAH, myelofibrosis Rheumatoid arthritis, Chronic myelogenous leukemia, Autoimmune thrombocytopenia, Chronic immune thrombocytopenia, Metastatic colorectal cancer, Cholangiocarcinoma, Acute myeloid leukemia FLT3 mutant, Mantle cell lymphoma, chronic lymphocytic leukemia, Chronic Myelogenous Leukemia, Acute myeloid leukemia (AML), Breast Cancer, Solid tumours with NTRK fusions, Activated phosphoinositide 3-kinase delta syndrome (APDS), PASLI (p110 delta activating mutation causing senescent T cells), lymphadenopathy, immunodeficiency, Thyroid cancer (DTC) kidney cancer, ALK+ve met NSCLC, MHER2-positive breast cancer, Acute myeloid leukemia (FLT3 mutation-positive), NSCLC with EGFR mutations, HER2-positive breast cancer, Glaucoma (topical), Chronic Myelogenous Leukemia, cell carcinomas of the head and neck, Idiopathic pulmonary fibrosis, Soft tissue sarcoma, T790M+ve NSCLC, mantle cell lymphoma CLL, SLL, T790M+ve NSCLC, Myelofibrosis, Advanced (metastatic) breast cancer EGFR colorectal cancer, Malignant glioblastoma, Renal cancer, Rheumatoid arthritis, Cholangiocarcinoma with FGFR2 fusionA, HER2-positive breast cancer, Tenosynovial giant cell tumor, Mantle Cell Lymphoma, Chronic Myelogenous Leukemia, ALL, Met RET fusion+ve NSCLC MTC, Breast cancer, Acute myeloid leukemia, Chronic Myelogenous Leukemia, MNSCLC colorectal cancer, Clorectal Cancer GIST, HCC, Advanced (metastatic) breast cancer HR+, HER2-ve, Glaucoma ocular hypertension, Advanced GIST Mastocytosis, Severe alopecia, Myelofibrosis, Adenocarcinoma, NSCLC, NSCLC, MTC, thyroid cancers, Neurofibromatosis type 1, Solid tumors, Renal Cancer HCC, KRAS non-small-cell lung cancer, Renal Cancer, Imatinib resistant GIST, Advanced pancreatic NET, Advanced Renal Cell Carcinoma, PTCL, breast cancer, Metastatic NSCLC, Chronic myelogenous leukemia, Actinic keratosis, Advanced RCC, Rheumatoid arthritis, M-Melanoma with BRAFV600E, EGFR breast cancer, SCLC chemo myelo preservation, HER2-positive breast cancer, Marginal zone lymphoma, Rheumatoid arthritis, Thyroid Cancer, Metastatic Melanoma BRAFV600E, Acute myeloid leukemia, and mantle cell lymphoma; or wherein a cell in a target tissue is a cancer cell or a cell located within a tumor; or further comprising, releasing an active agent within a cell in a target tissue by passing the composition into an interior of the target tissue.

\* \* \* \* \*